(12) United States Patent
Davis et al.

(10) Patent No.: US 11,017,886 B2
(45) Date of Patent: May 25, 2021

(54) HEALTH INFORMATION EXCHANGE SYSTEM AND METHOD

(71) Applicant: Peter Chang Enterprises, Inc., Farmington Hills, MI (US)

(72) Inventors: Brandon Davis, Novi, MI (US); Jeffrey Chang, West Bloomfield, MI (US)

(73) Assignee: PETER CHANG ENTERPRISES, INC., Farmington Hills, MI (US)

( * ) Notice: Subject to any disclaimer, the term of this patent is extended or adjusted under 35 U.S.C. 154(b) by 206 days.

(21) Appl. No.: 14/045,609

(22) Filed: Oct. 3, 2013

(65) Prior Publication Data

US 2014/0100875 A1 Apr. 10, 2014

Related U.S. Application Data

(60) Provisional application No. 61/709,676, filed on Oct. 4, 2012.

(51) Int. Cl.
*G16H 10/60* (2018.01)
*G06F 19/00* (2018.01)

(52) U.S. Cl.
CPC .............. *G16H 10/60* (2018.01); *G06F 19/00* (2013.01)

(58) Field of Classification Search
CPC ........ G06F 19/322; G06F 17/30; G06F 19/30; G06F 19/32; G06F 19/321; G06F 19/324;
(Continued)

(56) References Cited

U.S. PATENT DOCUMENTS

| 2008/0021730 A1* | 1/2008 | Holla | G16H 40/67 705/2 |
| 2008/0021741 A1* | 1/2008 | Holla | G16H 10/60 705/3 |

(Continued)

OTHER PUBLICATIONS

Informatics Corporation of America. CareAlign Solutions webpage, © 2013. Accessed Oct. 10, 2013 at www.icainformatics.com.
(Continued)

*Primary Examiner* — Michael Tomaszewski
*Assistant Examiner* — Jay M. Patel
(74) *Attorney, Agent, or Firm* — Foley & Lardner LLP

(57) ABSTRACT

A system, method and program product, the system comprising: memory comprising one or more non-transitory computer-readable media comprising: a master patient database; an exchange partner database; a sub-network database; and a global identifier database storing a plurality of global identifiers; and one or more computers configured with: an inbound module for receiving incoming request data or results data from an exchange partner, including a sub-process to determine when one of a plurality of methods is identified by the incoming data, a sub-network and/or one or more responding exchange partners, a requested data type, and whether a patient is identified; a sub-process to create when the incoming data is destined for a different exchange partner, a respective communication manager sub-process for each of the one or more or responding exchange partners; an outbound request module that has a multi-level consent determination process, and a sub-process to create, by the one or more computers, a global identifier comprising a link between the respective responding exchange partner and the requesting exchange partner for an initial transfer of the data.

43 Claims, 9 Drawing Sheets

(58) Field of Classification Search
CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 50/22; G06Q 50/24; G06Q 40/08; G06Q 10/10; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00
See application file for complete search history.

(56) References Cited

U.S. PATENT DOCUMENTS

| | | | | |
|---|---|---|---|---|
| 2008/0263050 A1* | 10/2008 | Randazzo | ........... | G06F 16/9535 |
| 2009/0012817 A1* | 1/2009 | Squires | .................. | G06Q 10/10 705/3 |
| 2009/0299767 A1* | 12/2009 | Michon | .................. | G16H 50/80 705/3 |
| 2010/0198755 A1* | 8/2010 | Soll | ........................ | G16H 10/60 706/11 |
| 2010/0274584 A1* | 10/2010 | Kim | ....................... | G16H 10/60 705/3 |
| 2010/0324927 A1* | 12/2010 | Tinsley | .................... | G06N 5/04 705/2 |
| 2011/0077973 A1* | 3/2011 | Breitenstein | ........... | G06Q 10/10 705/3 |
| 2012/0084092 A1* | 4/2012 | Kozuch | .................. | G16H 10/60 705/2 |
| 2012/0203571 A1 | 8/2012 | Crapo et al. | | |
| 2013/0024382 A1* | 1/2013 | Dala | .................... | G06F 21/6245 705/51 |
| 2013/0054467 A1* | 2/2013 | Dala | ...................... | G06Q 10/00 705/51 |

OTHER PUBLICATIONS

Covisint Corporation. Healthcare webpage, © 2013. Accessed Oct. 10, 2013 at www.covisint.com.

Optuminsight. OPTUMInsight webpage, © 2013. Accessed Oct. 10, 2013 at www.optuminsight.com.

\* cited by examiner

Fig. 5

HEALTH INFORMATION EXCHANGE SYSTEM AND METHOD

CROSS REFERENCE TO RELATED APPLICATION

This application claims priority from Provisional U.S. Application 61/709,676 filed Oct. 4, 2012, which is incorporated herein by reference in its entirety as if fully set forth herein.

BACKGROUND OF THE INVENTION

The present invention relates to the field of health care information exchange.

There is a need for improving on the available mechanisms for obtaining and exchanging physical and/or behavioral health care information in an evolving privacy environment and with the technical systems and protocols of the various health care providers being a moving target. The present invention accomplishes this.

BRIEF SUMMARY OF THE INVENTION

Embodiments of the invention may comprise a system, comprising: memory comprising one or more non-transitory computer-readable media comprising: a master patient database with patient consents; an exchange partner database with exchange partner data; a sub-network database listing exchange partner sub-networks, with each sub-network identifying exchange partners in the sub-network and a set of common processes for communicating between the exchange partners in the respective sub-network, and further comprising data for one or more contracts for the respective sub-network, with respective effective date information for both the one or more contracts and effective dates for respective patient consents for the respective sub-network and/or one or more exchange partners within the sub-network; and a global identifier database storing a plurality of global identifiers. The system further comprises one or more computers configured with: an inbound module for receiving, by the one or more computers and the one or more communications networks, incoming request data or results data from an exchange partner, including the following sub-processes: a sub-process to receive, by the one or more computers via one or more communications networks, the incoming request data or results data from the exchange partner; a sub-process to determine, by the one or more computers, when one of a plurality of methods is identified by the incoming data, a sub-network and/or one or more responding exchange partners, a requested data type, and whether a patient is identified; a sub-process to create, by the one or more computers, when the incoming data is destined for a different exchange partner, a respective communication manager sub-process for each of the one or more or responding exchange partners; an outbound request module for processing, by the one or more computers, an incoming request from a requesting exchange partner or internal process to send/obtain data, with sub-processes comprising: the respective communication manager sub-process for a respective one of the responding exchange partners configured to determine, by the one or more computers, if there is an active sub-network exchange partner relationship contract between the requesting exchange partner and the determined sub-network or between the requesting exchange partner and the one or more responding exchange partners, including when the requesting exchange partner is part of an affiliated parent organization in the determined sub-network, determining if the affiliated organization has request rights for the identified sub-network; the respective communication manager sub-process for a respective one of the responding exchange partners configured to determine if there is an active consent to communicate between the requesting exchange partner and the respective responding exchange partner including, when the responding exchange partner is part of an affiliated parent organization in the determined sub-network, determining if the affiliated organization is subject to the active consent; the respective communication manager sub-process for the respective one of the responding exchange partners configured to determine an active consent from the specified patient for the specified sub-network which consent authorizes the responding exchange partner directly or indirectly via a parent organization in the sub-network, to communicate patient data to the requesting exchange partner; the respective communication manager sub-process for the respective one of the responding exchange partners configured to determine a communication process for the responding exchange partner; the respective communication manager sub-process for the respective one of the responding exchange partners configured to manage outgoing communications with the respective responding exchange partner; and a sub-process to create, by the one or more computers, a global identifier comprising a link between the respective responding exchange partner and the requesting exchange partner for an initial transfer of the data.

In embodiments, the one or more computers may further be configured with: a patient chart module for accessing patient data, with the patient chart module comprising a break-the-glass functionality for accessing patient data triggered when one or more parameters are met; a sub-process to translate, by the one or more computers, data from the incoming request into first translated data in a system format; and a sub-process to translate, by the one or more computers, the data translated to the system format into second translated data in a format understandable by the responding exchange partner, or the requesting exchange partner, and to transmit, via the one or more communications networks, the second translated data to the responding exchange partner or the requesting exchange partner in a format it can understand.

In embodiments, the memory may further comprise a master staff index comprising for each of the exchange partners one or more staff; and wherein the one or more computers are further configured to access the master staff index and identify and map the communication to one or more of the staff identified for the specified responding exchange partner.

In embodiments, the sub-processes in the outbound request module for determining an active patient consent and an active sub-network exchange partner relationship contract effective between the requesting exchange partner and the determined sub-network or effective between the requesting exchange partner and the one or more responding exchange partners, determines if a date is within an effective date period in the patient consent and the relationship contract.

In embodiments, the one or more computers may further be configured with a delay queue process for stacking one or more transfers for a respective one of the exchange partners, when the respective exchange partner is unavailable or when a transfer exceeds a data limit.

In embodiments, the global identifier may be assigned based on the method called, a direction, and the exchange partners it is from and to, and the global identifier may be transmitted to both the requesting exchange partner and the responding exchange partner.

In embodiments, the one or more computers may further be configured with a sharing module configured with the following sub-processes: a sub-process for receiving, via the one or more communications networks, a request for data sharing of given data from a first exchange partner; a sub-process for caching in a cache, by the one or more computers, the given data; a sub-process for receiving, via the one or more communications networks, a request for data sharing of the given data from a second exchange partner; a sub-process for transmitting, by the one or more computers via the one or more communications networks, the given data to the second exchange partner from the cache; and a sub-process for transferring, by the one or more computers, via the one or more communications networks, the given data.

In embodiments, the one or more computers may further comprise a transportation module comprising a plurality transportation protocols, and wherein the sub-process to transmit connects to the transportation module, which is configured to select a transportation protocol based at least in part on communications requirements of the responding exchange partner.

In embodiments, one or more of the patient consents in the master patient database may be limited to specific data types; and the communications manager sub-process may be configured to determine whether there is a patient consent for the type of data requested in the request.

In embodiments, the one or more computers may further be configured with a process to transmit data updates using the global identifier, when triggered.

In embodiments, the one or more computers may further comprise a parsing module configured to parse the incoming request, when it does not identify a method, and to select a method based on data in the incoming request.

In embodiments, the incoming request may be contained in one selected from the group of an email, a Direct Message, a file in a file server.

In embodiments, the method identified may be associated with one of the sub-networks, and wherein the sub-process to create a communication manager sub-process creates a respective communication manager sub-process for each of a plurality of responding exchange partners and their one or more affiliated organizations.

In embodiments, the sub-process to create the global identifiers may only create a global identifier when the method determined is a predetermined method from a set of predetermined methods in the plurality of methods.

In embodiments, the one or more computers may be configured with a process to transmit data updates using the global identifier, when triggered by one or more parameters.

In embodiments, the different sub-networks may not communicate with each other unless there is data on a contract between the sub-networks.

In embodiments, the system may comprise an interface configured to create, revoke, modify, manage, reconcile, receive, interpret, or transmit the consents.

In embodiments, the one or more computers are configured to verify the identity of a person or entity through an electronic interface.

In embodiments, the interface comprises a graphical user interface.

In embodiments, the interface comprises one or more electronic interfaces or APIs for machine-to-machine interaction.

In embodiments, a method is disclosed, comprising: accessing, by one or more computers, one or more non-transitory computer-readable media comprising: a master patient database with patient consents; an exchange partner database with exchange partner data; a sub-network database listing exchange partner sub-networks, with each sub-network identifying exchange partners in the sub-network and a set of common processes for communicating between the exchange partners in the respective sub-network, and further comprising data for one or more contracts for the respective sub-network, with respective effective date information for both the one or more contracts and effective dates for respective patient consents for the respective sub-network and/or one or more exchange partners within the sub-network; a global identifier database. The method may further comprise an optional step of accessing patient data, by the one or more computers, triggered when one or more break-the-glass parameters are met; a sub-step of receiving, by the one or more computers via one or more communications networks, incoming request data or results data from an exchange partner; a sub-step of determining, by the one or more computers, when one of a plurality of methods is identified by the incoming data, a sub-network and/or one or more responding exchange partners, a requested data type, and whether a patient is identified; a sub-step of creating, by the one or more computers, when the incoming data is destined for a different exchange partner, a respective communication manager sub-process for each of the one or more or responding exchange partners; processing, by the one or more computers, an incoming request from a requesting exchange partner or internal process to send/obtain data, with sub-processes comprising sub-steps: a sub-step for a respective one of the responding exchange partners of determining, by the one or more computers, if there is an active sub-network exchange partner relationship contract between the requesting exchange partner and the determined sub-network or between the requesting exchange partner and the one or more responding exchange partners, including when the requesting exchange partner is part of an affiliated parent organization in the determined sub-network, determining if the affiliated organization has request rights for the identified sub-network; a sub-step for a respective one of the responding exchange partners of determining if there is an active consent to communicate between the requesting exchange partner and the respective responding exchange partner including, when the responding exchange partner is part of an affiliated parent organization in the determined sub-network, determining if the affiliated organization is subject to the active consent; a sub-step for the respective one of the responding exchange partners of determining an active consent from the identified patient for the specified sub-network which consent authorizes the responding exchange partner directly or indirectly via a parent organization in the sub-network, to communicate patient data to the requesting exchange partner; a sub-step for the respective one of the responding exchange partners of determining a communication process for the responding exchange partner; a sub-step for the respective one of the responding exchange partners of managing outgoing communications with the respective responding exchange partner; and a sub-step of creating, by the one or more computers, a global identifier comprising a link between the respective responding exchange partner and the requesting exchange partner for an initial transfer of the data.

In embodiments, the method may comprise accessing, by the one or more computers, one or more non-transitory computer-readable media comprising a patient consent database.

In embodiments, the method may comprise transmitting consent information, via the one or more computers, in a standard or non-standard structured data format.

In embodiments, the method may comprise transmitting consent information, via the one or more computers, in a human-readable image.

In embodiments, the method may comprise receiving consent information, via the one or more computers, in a standard or non-standard structured data format, parsing the received consent and storing in the patient consent database, and making such received consent available for processing by the one or more computers.

In embodiments, the method may comprise receiving consent information, via the one or more computers, in a human readable image, and making such received consent available to the one or more computers.

In embodiments, the method may comprise receiving and parsing electronic requests for consent information, via the one or more computers, from an exchange partner and responding thereto.

In embodiments, the method may comprise receiving and parsing electronic requests for consent information, via the one or more computers, from an exchange partner and responding thereto.

In embodiments, the method may comprise revoking one or more consents at the request of a user or exchange partner which submits such request electronically through an electronic interface or through a human interaction with a graphical user interface with the one or more computers, and processing the revocation of such consents.

In embodiments, the method may comprise the revocation may be effective on one or more revocation criteria, which are specified through the revocation request or based on configured rules, through which the one or more computers may determine the consents that match the revocation criteria and revoke those matched consents.

In embodiments, the method may comprise transmitting, via the one or more computers, a request, including a revocation request, to exchange partners.

In embodiments, the method may comprise parsing, via the one or more computers, the consent information contained in the consent database, interpreting the parsed consent information, and logically consolidating the consent information in one or more formats.

In embodiments, the method may comprise transmitting or displaying, via the one or more computers, the logically consolidated consent information.

In embodiments, the method may comprise processing, via the one or more computers, one or more actions on one or more consents based on the logically consolidated consent information.

In embodiments, a program product is disclosed, comprising: one or more non-transitory computer-readable media, comprising computer code embodied therein that when executed by one or more computers, performs the steps: accessing, by one or more computers, one or more non-transitory computer-readable media comprising: a master patient database with patient consents; an exchange partner database with exchange partner data; a sub-network database listing exchange partner sub-networks, with each sub-network identifying exchange partners in the sub-network and a set of common processes for communicating between the exchange partners in the respective sub-network, and further comprising data for one or more contracts for the respective sub-network, with respective effective date information for both the one or more contracts and effective dates for respective patient consents for the respective sub-network and/or one or more exchange partners within the sub-network; a global identifier database. The method may further comprise an optional step of accessing patient data, by the one or more computers, triggered when one or more break-the-glass parameters are met; a sub-step of receiving, by the one or more computers via one or more communications networks, incoming request data or results data from an exchange partner; a sub-step of determining, by the one or more computers, when one of a plurality of methods is identified by the incoming data, a sub-network and/or one or more responding exchange partners, a requested data type, and whether a patient is identified; a sub-step of creating, by the one or more computers, when the incoming data is destined for a different exchange partner, a respective communication manager sub-process for each of the one or more or responding exchange partners; processing, by the one or more computers, an incoming request from a requesting exchange partner or internal process to send/obtain data, with sub-processes comprising sub-steps: a sub-step for a respective one of the responding exchange partners of determining, by the one or more computers, if there is an active sub-network exchange partner relationship contract between the requesting exchange partner and the determined sub-network or between the requesting exchange partner and the one or more responding exchange partners, including when the requesting exchange partner is part of an affiliated parent organization in the determined sub-network, determining if the affiliated organization has request rights for the identified sub-network; a sub-step for a respective one of the responding exchange partners of determining if there is an active consent to communicate between the requesting exchange partner and the respective responding exchange partner including, when the responding exchange partner is part of an affiliated parent organization in the determined sub-network, determining if the affiliated organization is subject to the active consent; a sub-step for the respective one of the responding exchange partners of determining an active consent from the identified patient for the specified sub-network which consent authorizes the responding exchange partner directly or indirectly via a parent organization in the sub-network, to communicate patient data to the requesting exchange partner; a sub-step for the respective one of the responding exchange partners of determining a communication process for the responding exchange partner; a sub-step for the respective one of the responding exchange partners of managing outgoing communications with the respective responding exchange partner; and a sub-step of creating, by the one or more computers, a global identifier comprising a link between the respective responding exchange partner and the requesting exchange partner for an initial transfer of the data.

BRIEF DESCRIPTION OF THE DRAWINGS

Figure 5:
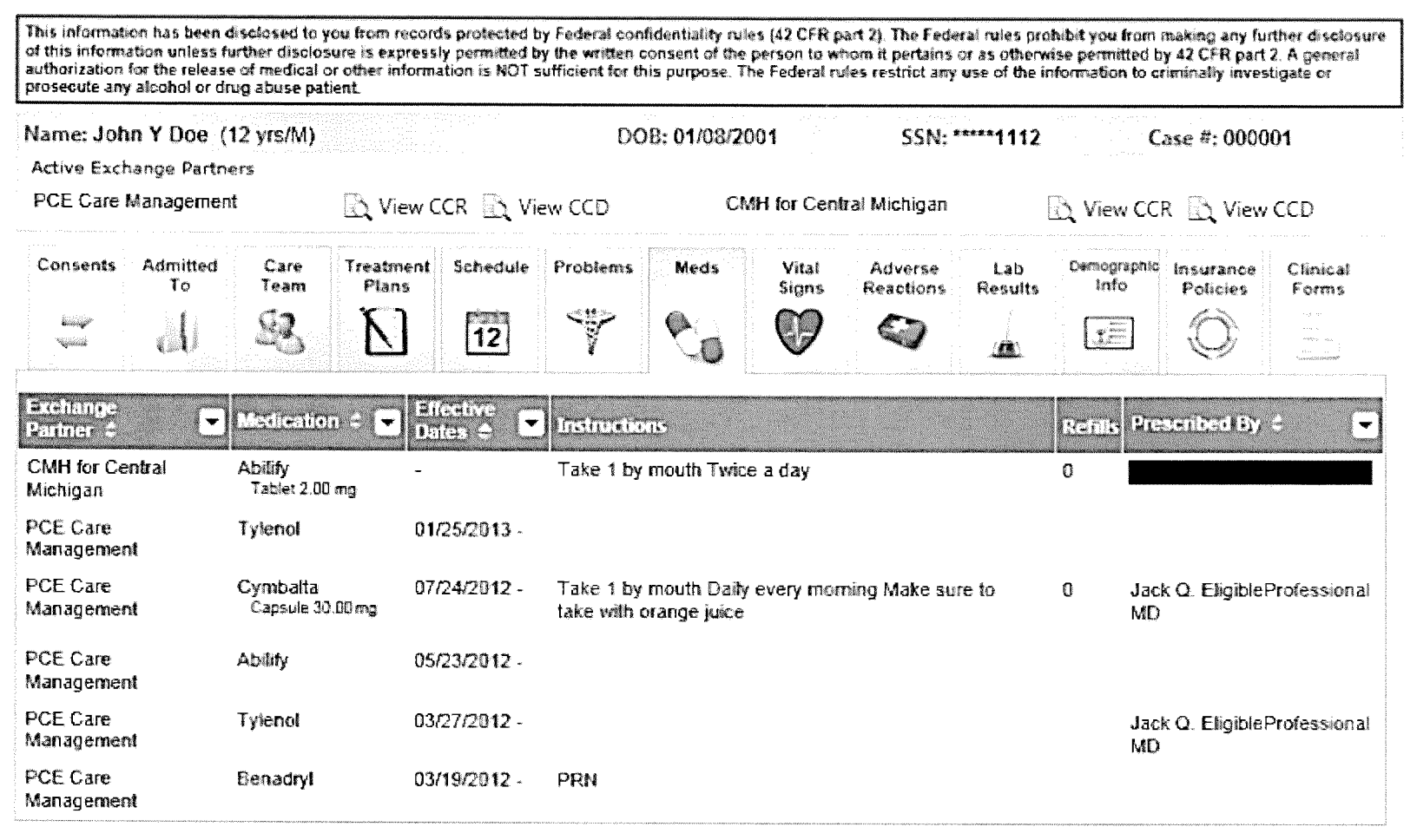

FIG. 5 illustrates an exemplary screenshot of an exchange partner interface for selecting patient data.

DETAILED DESCRIPTION OF EMBODIMENTS

Figure 1:
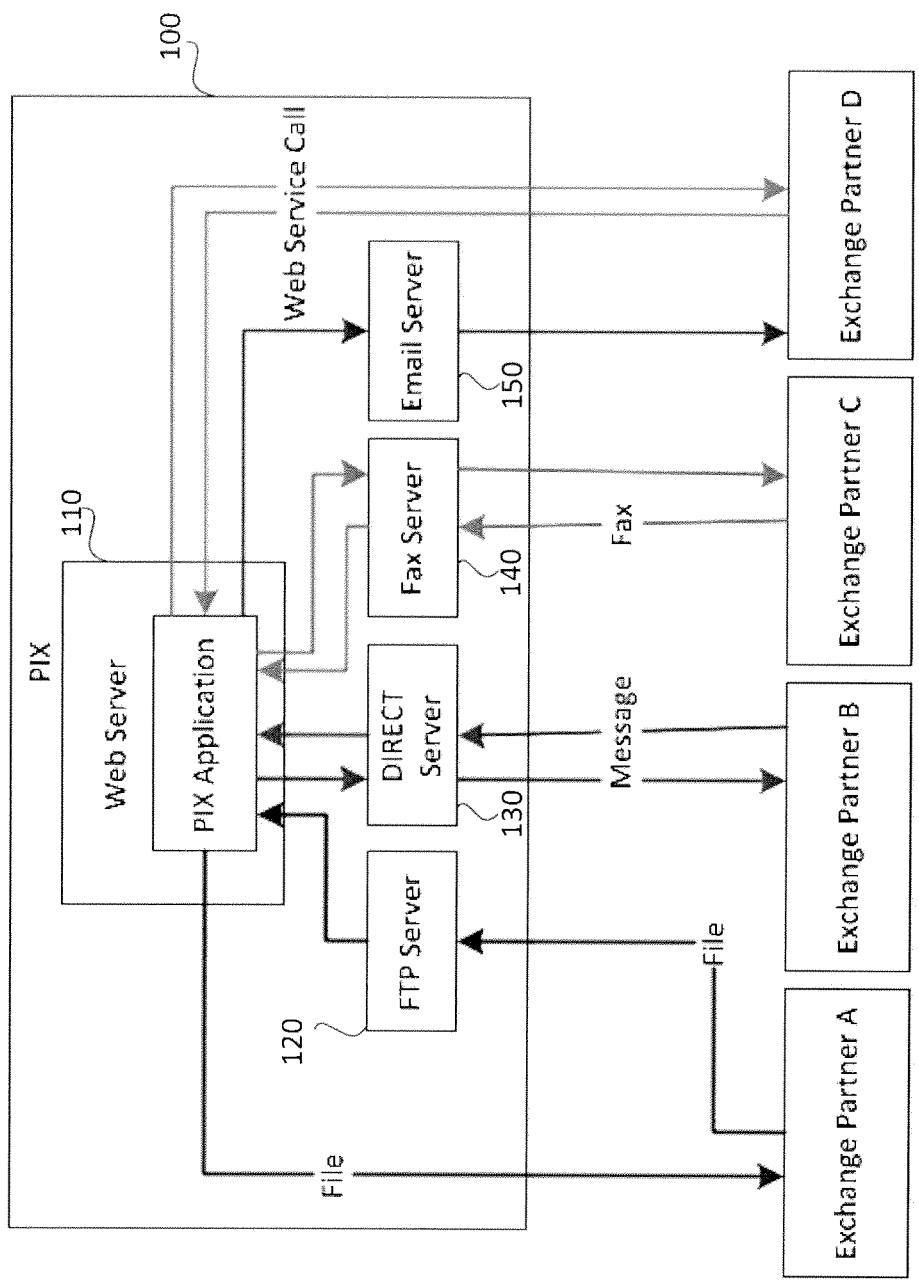
FIG. 1 is a diagram of an embodiment of a system server configuration.

The following description is presented to enable a person of ordinary skill in the art to make and use the invention, and is provided in the context of particular applications and their requirements. Various modifications to the embodiments will be readily apparent to those skilled in the art, and the generic principles defined herein may be applied to other embodiments and applications without departing from the spirit and scope of the invention. Moreover, in the following description, numerous details are set forth for the purpose of explanation. However, one of ordinary skill in the art will realize that the invention might be practiced without the use of these specific details. In other instances, well-known structures and devices are shown in block diagram form in order not to obscure the description of the invention with unnecessary detail. Thus, the present invention is not intended to be limited to the embodiments shown, but is to be accorded the widest scope consistent with the principles and features disclosed herein.

While the invention is described in terms of particular examples and illustrative figures, those of ordinary skill in the art will recognize that the invention is not limited to the examples or figures described. Those skilled in the art will recognize that the operations of the various embodiments may be implemented using hardware, software, firmware, or combinations thereof, as appropriate. For example, some processes can be carried out using processors or other digital circuitry under the control of software, firmware, or hardwired logic. (The term "logic" herein refers to fixed hardware, programmable logic and/or an appropriate combination thereof, as would be recognized by one skilled in the art to carry out the recited functions.) Software and firmware can be stored on computer-readable storage media. Some other processes can be implemented using analog circuitry, as is well known to one of ordinary skill in the art. Additionally, memory or other storage, as well as communication components, may be employed in embodiments of the invention.

The following terms used herein have the following definitions:

Exchange Partners—Entities which can communicate electronically with present system. Embodiments of the system may track electronic service information (for example, an organization's OID), legal information, application URLs, type, logging parameters, contact information, mapping information for other exchange partners (For example when receiving information from another exchange partner, what is the identifier to be sent to this exchange partner so that it understands who the information is from. In the opposite direction, this is the identifier of which exchange partner data is meant for. In short the system maps a different exchange partner's record to an identifier defined by this exchange-partner and maps it back-and-forth)

Organization—A grouping of exchange partners, other organizations, or an individual exchange partner. This may be stored in a tree-structure such that end-nodes are always an exchange partner.

Method—A particular action supported by the system, which an exchange partner can invoke on the system (inbound) and/or the system can invoke on an exchange partner (outbound). An inbound method may result in 0 or more methods being executed outbound to 0 or more different exchange partners. A method may also be triggered by a scheduled/automated or manual process within the system.

Network—A group of methods and rules defining their use. Rules include the direction which the method can be called relative to the system (inbound/outbound/both/neither).

Sub-Network—A network specific to a set of exchange partners having a legal agreement between them to communicate using a set of common electronic methods. Methods and their defining rules are restricted to the parent network's methods/rules, but can be more restrictive. Communication cannot occur across networks or sub-networks unless configured based on agreements between the entities in control of the sub-networks. Generally the sub-network may be given a name known by all parties involved.

For example the system may define a network for communicating with "Personal Health Record" or "PHR" applications, which includes methods applicable to all PHR applications. The system would define one sub-network for each PHR application comprising the exchange partners feeding the PHR application. In embodiments, none of the PHR sub-networks are aware of each other. In other embodiments, the PHR sub-networks are completely aware or partially aware of other sub-networks.

Contract—A date-based authorization based on a legal agreement identifying and allowing one or more organizations to communicate with one or more another organization through the system within a particular sub-network. In embodiments, organizations may only communicate with the system when they have an active contract.

Consent—A date-based authorization based on a legal agreement signed by a person, which allows one or more exchange partners to share that person's personal information (defined in the consent) to other exchange partners within a sub-network. The consent may be between any subset of the exchange partners within the sub-network or all of the exchange partners in the sub-network. Permitted exchange partners are typically defined by the signer and, in some embodiments, may be revoked by the signer at any time. They also may have an automatic expiration, which becomes effective after a given period of time. The system provides methods for maintaining consents including the ability to create, revoke, manage, and reconcile consents. The system also allows the receipt, transmission, and interpretation of consents in standard (e.g., XACML) and non-standard formats. A consent may also be a "negative consent", which prohibits, rather than authorizes, the sharing of a person's information.

In embodiments, consents may be restricted to contracts. So if a particular exchange partner is consented for a given person, but the exchange partner's contract within the sub-network is expired, personal information can no longer be sent to/received from that exchange partner.

Communication Parameters—Information tied to a particular exchange partner and sub-network which identifies the transportation protocols used by this exchange partner to communicate with the system (inbound) and also how the system communicates with this exchange partner (outbound). In embodiments, transportation protocols supported include Web Services (SOAP, REST, etc.), socket connections, MLLP, secure FTP, DIRECT secure e-mail. In embodiments, protocol support may be modularized and additional protocols may be added as necessary. The information also includes data required for the specific transportation protocols such as user names, passwords, URLs, port numbers and other server information. Other information that may be recorded include optional code modules which may contain exchange-partner-specific code that is used to deal with non-standard data and other non-standard procedures. (For example, pulling misplaced data out of an HL7 message, or intentionally putting data in a non-standard location to meet the requirements/expectations of the exchange partner.) These code modules also can define different forms of the data sent to/received from the exchange partner, like HL7, XML, Base64, etc. Thus, in embodiments the system may be protocol agnostic.

For example a particular exchange partner may initiate communications with the system via Web Services using HL7, while the system may only initiate communications with the exchange partner using a socket using XML.

Global Identifiers—Some methods involve sending data from one exchange partner to another which must be linked across the exchange partners. In embodiments, a global identifier may be used to accomplish this link. In embodiments, the global identifier may be assigned to data (usually a particular record/data set) by the system based on the method being called, the direction, the exchange partner it is from/to and the sub-network. In embodiments, the global ID is sent back to the sending exchange partner and sent to the receiving exchange partner. Thus, in embodiments, with a given a global ID, a record may be tracked across all systems involved. Furthermore, in embodiments records may be synchronized over time. For example an appointment record which was sent from exchange partner A to another exchange partner B may be stored by exchange partner B. Later when that same appointment is updated in A (for example, if it is cancelled) the same record may be sent again to B using the Global ID to synchronize the record to the updated record from A. Whether global IDs are used for a particular exchange of data may be based at least in part on the exchange partners involved, the sub-network, and the methods. (In embodiments, a data transfer may use a global ID when the intent is that the data will be stored at the destination. In embodiments, when the data is not to be stored at/linked to the destination, then a sharing protocol may be used that does not have a global ID.)

Delayed Transactions—The system provides a delayed transaction queue (delay queue) which stores data being transmitted when an exchange partner is unavailable or is not responding. In embodiments, the sending system may receive a notification that the destination is unavailable and the transmission will be automatically tried again in a fixed period of time. In the meantime, additional transfers to the "down" exchange partner may be stacked up in the delayed transaction queue. When the destination "comes back up", delayed transmissions will be retried in the order they were received.

In embodiments, another way that a transmission may end up in the delay queue is if a maximum data limit is reached. Limits may be defined to prevent exchange partners from being overloaded with too much data in a short period of time. For example, a limit might be set which prevent more than 50 records from being sent to an exchange partner at a time. The result is that if 60 records are sent from an exchange partner at the same time, in embodiments, the system may divide the records into two sets: the first set of 50 records will be sent immediately while second set containing the remaining 10 records will be put into the delay queue and sent later. (Again, notification is sent to the sending exchange partner that a delay has taken place but nothing needs to be done).

Data Caching—In embodiments, for data sharing (when requested data is not expected to be stored by/linked with the requestor), a caching process may be turned on within the system to prevent the same requests from hitting the source system within a short time period. This caching process may be used to prevent unnecessary traffic and processor time when the same data would just be returned over and over.

Access logging—In embodiments, all method calls inbound and outbound may be logged and the parameters of those methods may be serialized in the logs. In embodiments, the logs may include the method called, sub-network, parameters of the method, direction it was called in, which exchange partner it was from/to, the user name from within the exchange partner which initiated the communication, and other metadata. Additionally, in embodiments there may be a parameter on the exchange partner which turns on full logging. This configuration operates to serialize and store everything including the data being sent/received.

Error Handling—Embodiments of the system process includes extensive error handling which includes the sending of various levels of error, warning, and informational messages from one exchange partner to another as well as to/from the system. For example error messages may identify a data set not being accepted by the destination system or the system itself because it fails validation criteria. In embodiments, messages may be displayed in all systems involved and may be used to control data that should be re-sent (either manually by a person, or automatically by an automated process).

Patient Chart—Embodiments of the system provide a patient chart which shows all data for a patient known and, if necessary, consented within a sub-network. In embodiments, the chart may include optional 'break-the-glass' functionality for emergency situations for those who have access. For EHRs not having the capabilities to use the patient chart API, a lightweight-app that acts as a stand-in for the exchange partner exists. (See provisional patent application pages 23, 24 and 52-64.)

Master patient index—A listing of patients in a sub-network that have been reported by exchange partners within a sub-network. This listing index may be used in embodiments to link patients between systems. The system contains methods for adding and maintaining the patient records. One example use is for the Patient Chart.

Master staff index—A listing of staff in a sub-network that have been reported by exchange partners within a sub-network. This listing of staff may be used to link staff between systems. In embodiments, the system may contain methods for adding and maintaining the staff records. One example use is for sharing a staff's appointments across exchange partners so that a staff working for multiple entities sharing a sub-network in the system may view all of their appointments within either exchange partner's EHR.

Technical—In embodiments, web services capabilities are provided in the system. Other transportation protocols may operate differently. Examples discussed herein are specific to a process of communication between two exchange partners. A different scenario may involve one exchange partner communicating only with the system for example to maintain the master patient index. Another scenario may comprise one exchange partner communicating with another, where no response is required.

Referring to FIG. 1, there is shown an embodiment for implementing the present invention. An embodiment of the system of the present invention is represented by block 100. Embodiments of block 100 may comprise one or more communication servers such as a web server 110, an FTP server 120, a Direct server 130, a facsimile server 140, and an email server 150, to name a few of the communication servers that can be used. The invention is not limited to the type of communication server used. The Web server 110 is configured to communicate with exchange partner A, exchange partner B, exchange partner C, and exchange partner D via file, message, fax and web service call communications with the servers 110-150, to exchange health care information when various requirements are met. Note: servers involved are not necessarily comprehensive and more may be added as new inbound/outbound transportation modules are incorporated.

Figure 2:
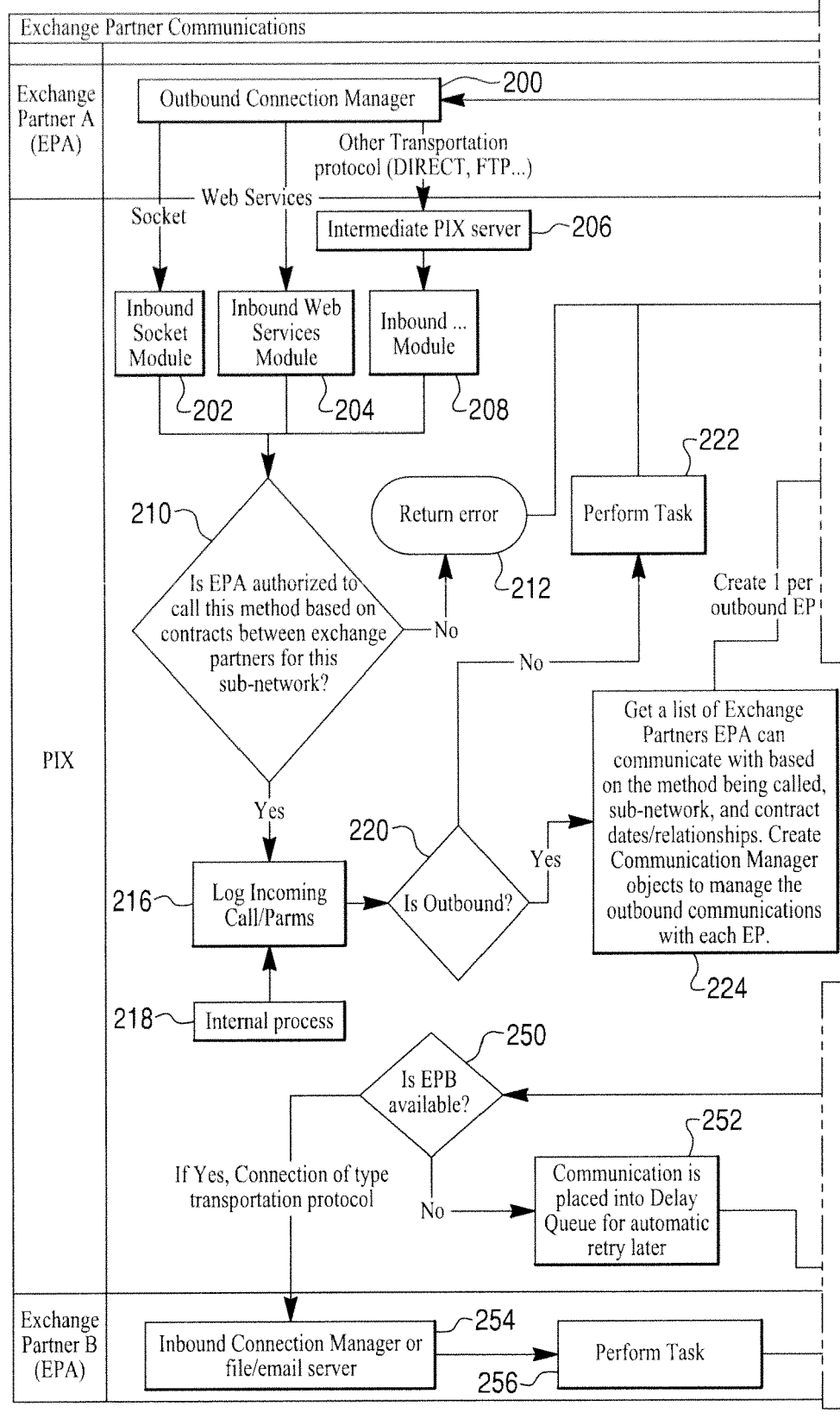
FIG. 2 illustrates an embodiment of an exemplary logic system.
Figure 2:
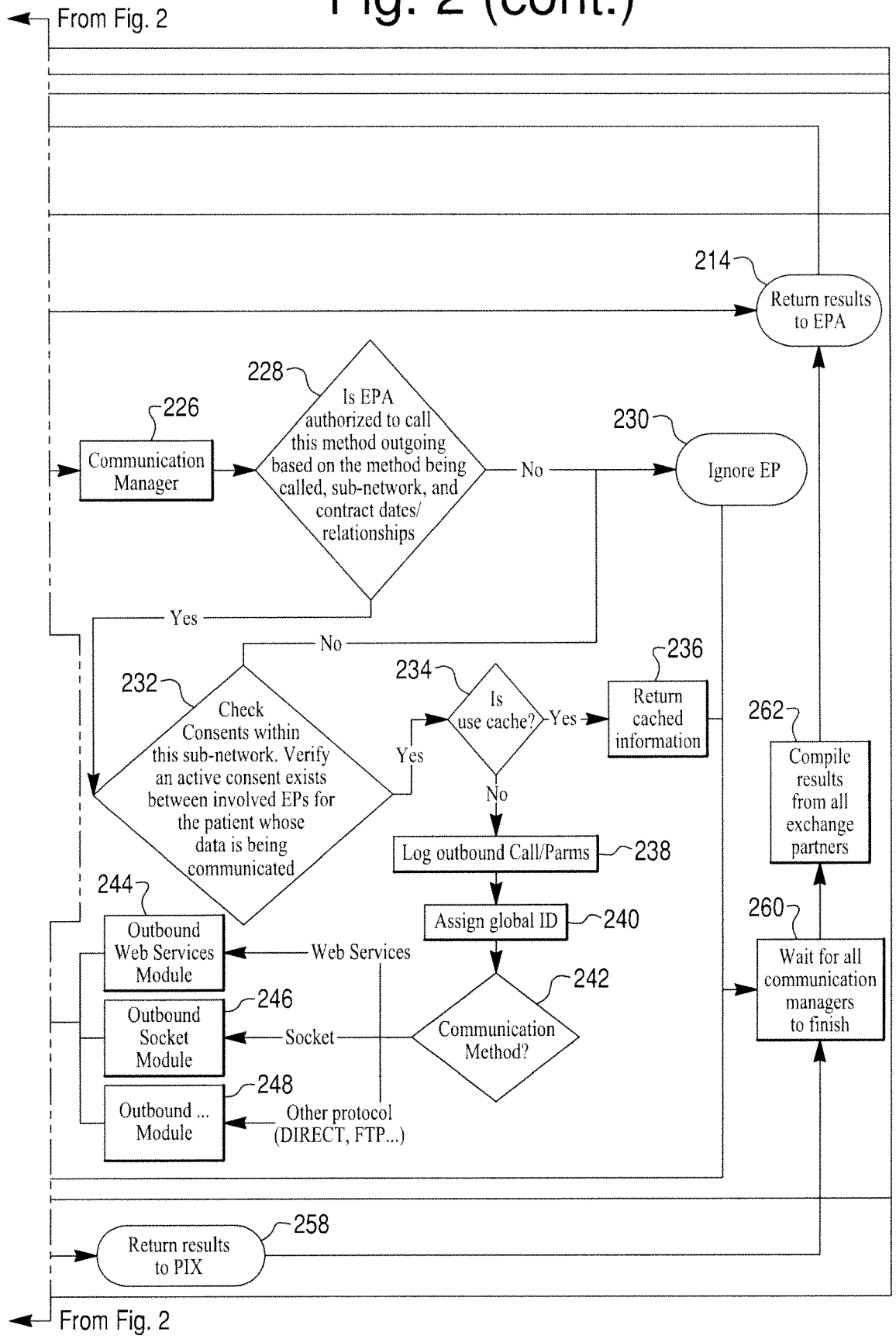
Figure 3:
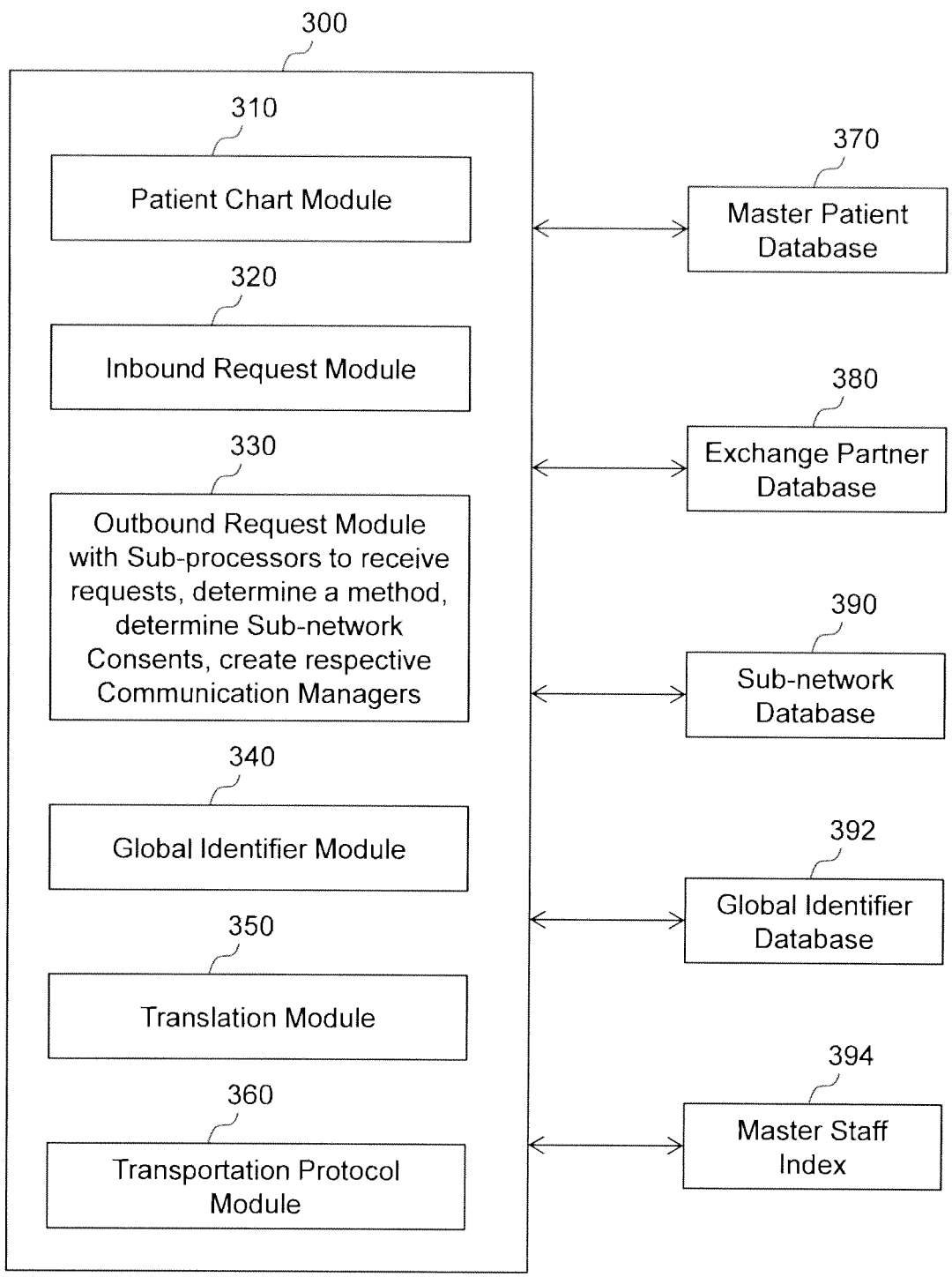
FIG. 3 illustrates an exemplary set of computer modules and databases.

Referring to FIG. 2, an exchange partner A (EPA) is illustrated communicating via an outbound connection manager Method 200 with the present system over a particular sub-network using one of any supported transportation protocols. (This may include an intermediate server within the present system depending on the protocol.)

Exchange partner A may be a $3^{rd}$ party electronic health records (EHR) system, a health information exchange (HIE) system, a Personal Health Record (PHR) system, or a light-weight application which can be used in cases where a $3^{rd}$ party system does not support the present system APIs (including standard APIs implemented within the present system).

A communication may also be started by an scheduled/automated or manual process internal to the present system.

An inbound socket module 202, an inbound web services module 204, and an inbound module 208 receiving other transportation protocol communications, e.g., Direct, FTP, etc.) via an intermediate server 206 represent the incoming communications to the system from exchange partner A.

An inbound module logic block 210 determines whether exchange partner A has identified a sub-network and whether it has access to communicate with the present system on this sub-network based on active contracts between itself and other exchange partners for this sub-network via data from one or more databases maintained by the system or maintained by a third party and accessed by the system. Contracts may be between two exchange partners/organizations on a sub-network and include effective dates. A contract is active when the current date falls within the contract's effective dates.

If exchange partner A is not authorized for this sub-network, then a return error message is generated and sent, as represented by logic block 212, and this result is returned to the to exchange partner A, as represented by logic block 214.

If exchange partner A is authorized to communicate with this sub-network, then the incoming communication is logged in block 216 and proceeds to the next step.

In logic block 220, it is determined whether the communication is meant for 0 or more other exchange partners based on the sub-network, an identified communication Method (if any), and the data specified within the communication. Note that the zero case would be when the communication is meant for present system, itself, e.g., as in registering a patient with the master patient index for example.

If No, then an action is performed in block 222, (e.g., an internal action such as registering a patient with the master patient index. This could result in writing to a database for example, within the present system) and a result is returned back to exchange partner A, as represented by logic block 214.

If the communication is meant for one or more exchange partners, then the logic proceeds to the next step, represented by logic block 224, wherein it is determined which exchange partners this communication is meant for based at least in part on the sub-network, and/or contracts among the exchange partners and contract effective dates, and/or the data identified in the requesting communication.

For each exchange partner, a communication manager is created, as represented by logic block 226. The respective communication manager will route the communication to its respective exchange partner destination based on pre-defined options and protocols specific to the exchange partner system. The respective communication managers for the different destination exchange partners operate in parallel.

Each communication manager logic determines whether exchange partner A is authorized to communicate with its outbound exchange partner destination, e.g., for example exchange partner B (EPB), as represented by logic block 230, based at least in part on the sub-network, communication method, and contract dates/relationships.

If No, no communication with exchange partner B occurs. This is represented by logic block 230.

If Yes, the logic moves to the next step and verifies in logic block 232, when consents are applicable to the sub-network and type of data being communicated, that an active consent exists for a patient involved in the requesting communication based on effective dates for the requesting and responding parties (e.g., an exchange partner or an organization within the exchange partner) involved in the communication. Relationships among organizations are also evaluated via tables or other data review to determine if a consent relating to a parent organization may apply to a subsidiary/related organization.

If No, the communication for exchange partner B is ignored and no communication with that exchange partner occurs, as represented by logic block 230.

If Yes, the logic proceeds to a next step and determine if caching is enabled for this communication method and it has been triggered, e,g., the requesting communication is for data sharing and has previously been generated and cached. This operation is represented by logic block 234. If Yes, the cached information is returned, as represented by logic block 236.

If No, then the logic proceeds to logic block 238 and outbound calls/parameters are logged.

Then in certain situations, e.g., for example, where a first transfer of data is to be stored at the requesting exchange partner or linked across the exchange partners, a global identifier for the communication/data involved may be generated and sent back to exchange partner A with the result as well as forwarded to exchange partner B so that all entities involved can track the transaction as well as resynchronize the data at a later time if desired. This operation is represented by logic block 240.

Then in logic block 242 the communication manager accesses a transportation module and obtains outbound communication parameters to use for the destination responding exchange partner B. For example, an outbound web services module 244, or an outbound socket module 246, or an outbound module 248 for other protocols (e.g., Direct, FTP) may be accessed for the communication to exchange partner B.

A communication is made to exchange partner B using the determined protocol and it is up the EPB to perform a task and optionally return a result back to EPA. Some protocols involve a connection which will return an immediate result, other protocols will return the information to a file/email server and a response may be sent at a later time.

The logic then determines if exchange partner B is unavailable (cannot be contacted or other technical problem), as represented by logic block 250. If exchange partner B is unavailable, then the communication may, depending on the sub-network configurations, be moved to a Delay Queue where it is stored and retried automatically at a later time. This operation is represented by logic blocks 252. A message is returned to EPA informing them of the situation.

When exchange partner B is available, then the requesting communication or data therefrom is provided via an inbound connection manager or file/email server to exchange partner B using the determined transportation protocol, as represented by logic block 254. Exchange partner B performs a task based on data from the requesting communication, as represented by logic block 256. The system may return a result, as represented by logic block 258, depending on the transportation protocol. For example, the system may not return a result if there is a technical problem either in the software at EPB or the network connections between EPB and the system; OR if the software at EPB was poorly written and lacks an ability to return a result (For example EPB may open a socket port and we may send data, but no response may come back even though there is not a technical problem.

The present system may, depending on the sub-network configurations and how many exchange partners in the sub-network will be responding, wait for all communication managers to return results or other messages. In embodiments, when all of the responding exchange partner have reported back, the results may be compiled into one data set. These operations are represented by logic blocks 260 and 262. In embodiments, results/messages from responding exchange partners may be sent back to EPA as they are received without waiting for other communication managers to return results.

Results are then returned to the requesting exchange partner A. The protocol used may depend on the original inbound protocol from requesting exchange partner A.

In embodiments of the system, one or more computers 300 may be configured with the following modules: a patient chart module 310 for accessing patient chart data, an inbound request module 320 for processing requests that have been cleared through the system, an outbound request module 330 for processing incoming requests in a consent driven manner to be described, a global identifier module 340 for assigning global identifiers, a translation module 350 for translating data formats so that a destination exchange partner can understand and process the data, and a transportation protocol module 360 for determining the correct transportation protocols to use for the various destination exchange partners. These various modules communicate with the databases 370-394. Note that other databases in or accessible to the system may comprise a data-point mapping database [tables for mapping/translating inbound/outbound data across systems to a form which is understandable by the responding exchange partner and vice versa] a definitions database, and a method database, to name a few.

The various databases may be stored on one or more non-transitory computer-readable media. The master patient index 370 comprises patient data that in embodiments may include patient demographic data, patient status data, and patient consents (which may be for a sub-network, or only for specific exchange partners in a sub-network, or only for selected data types). The exchange partner database 380 may comprise, in embodiments, exchange partner data such as electronic service information (e.g., OIDs), legal information, application URLs, type, logging parameters, mapping information for other exchange partners, to name a few.

The sub-network database 390 may comprise in embodiments data for each exchange partner sub-network, with the data for each sub-network identifying exchange partners in the sub-network and a set of common processes and access methods for communicating between the exchange partners in the respective sub-network. The sub-network database 390 may further comprise in embodiments, data for one or more contracts for the respective sub-network, or between exchange partners within the sub-network, with respective effective date information for the one or more contracts. The sub-network database may further comprise in embodiments, effective dates for respective patient consents for the respective sub-network or one or more exchange partners within the sub-network.

Note that in embodiments, the different sub-networks do not communicate with each other unless there is data on a contract between the sub-networks or a sub-network is an exchange partner in another sub-network.

The global identifier database 392 in embodiments may comprise a listing of global identifiers that are links in one direction from a responding exchange partner to the requesting exchange partner, and may be used in embodiments, to push or pull data updates back to the requesting exchange partner to synchronize data. The master staff index 394 comprises staff data that in embodiments, may include one or more of respective identifiers for staff in a sub-network, staff communication data, e.g., email addresses, telephone numbers, or message mapping to an API for staff in a patient's care-team, respective staff status and availability, staff demographics, to name a few.

Referring to the modules in block 300, the patient chart module 310 is configured with computer code to access patient data. In some embodiments, the patient chart module may comprise a break-the-glass functionality for accessing patient data, with the break-the-glass functionality triggered when one or more parameters are met.

The inbound request module 320 is configured with computer code to receive, via one or more communications networks, data results from a requesting exchange partner and for returning data results to the requesting exchange partner.

The inbound request module 320 is configured with computer code to process, by the one or more computers, an incoming request from a requesting exchange partner to obtain patient data for a specified patient, with multiple sub-processes, and to return results to a requesting exchange partner.

In embodiments, the inbound request module 320 comprises a sub-process to receive, by the one or more computers via one or more communications networks, the incoming request from the requesting exchange partner or results from a responding exchange partner.

In embodiments, the inbound request module 320 comprises a sub-process to determine, by the one or more computers, when one of a plurality of methods is identified by the incoming request, a sub-network and/or one or more responding exchange partners, a requested data type, and the patient.

In embodiments, the inbound request module 320 comprises a sub-process to determine, by the one or more computers, if there is an active sub-network exchange partner relationship contract between the requesting exchange partner and the determined sub-network or between the requesting exchange partner and the one or more responding exchange partners, including when the requesting exchange partner is an affiliated organization to a parent exchange partner in the determined sub-network, determining if the affiliated organization has request rights for the identified sub-network.

In embodiments, the inbound request module 320 comprises a sub-process to create, by the one or more computers, a respective communication manager sub-process for each of the one or more or responding exchange partners.

In embodiments, in an outbound module 330 the respective communication manager sub-process may be configured for a respective one of the responding exchange partners to determine if there is an active consent to communicate between the requesting exchange partner and the respective responding exchange partner including, when the responding exchange partner is an affiliated organization to a parent exchange partner that in the determined sub-network, determining if the affiliated organization is subject to the active consent.

In embodiments, in the outbound module 330 the respective communication manager sub-process may be configured to determine an active consent from the specified patient for the specified sub-network which consent authorizes the responding exchange partner directly or indirectly via a parent in the sub-network, to communicate patient data to the requesting exchange partner.

In embodiments, the respective communication manager sub-process may be configured to determine a communication process for the responding exchange partner.

In embodiments, the respective communication manager sub-process may be configured to manage outgoing communications with the respective responding exchange partner. In embodiments, this management function may comprise determining a responding communications method, determining correct data format translations so that the destination exchange partner system can understand and process the data, determining a transportation protocol for the responding exchange partner, (e.g., Direct, FTP, Web services, SOAP, etc.), compiling data from when there are multiple responding exchange partners and sending the data to the requesting exchange partner. In embodiments, the management function may comprise determining if the requested data includes a flag or other designator that the data cannot be disclosed, or only portions of the data can be disclosed.

In embodiments, the outbound request module 330 may comprise a sub-process to create, by the one or more computers, a global identifier comprising a link between the respective responding exchange partner and the requesting exchange partner for an initial transfer of the data requested, e.g., patient data, staff data, etc.

In embodiments, the outbound request module 330 may comprise a sub-process to translate, by the one or more computers, data from the incoming request into first translated data in a format understandable by the respective responding exchange partner, and to transmit via the one or more communications networks, the first translated data to the responding exchange partner using the correct transportation protocol.

In embodiments, the outbound request module 330 may comprise a sub-process to translate, by the one or more computers, the data from the respective responding exchange partner into second translated data in a format understandable by the requesting exchange partner, and to transmit, via the one or more communications networks, the second translated data to the requesting exchange partner in a format it can understand and using the correct transportation protocol.

In embodiments, the system may further comprise or have access a master staff index comprising for each of the exchange partners one or more staff with staff data, and may further comprise the one or more computers being further configured to access the master staff index and identify and map the communication to one or more of the staff identified for the specified responding exchange partner.

In embodiments, the sub-processes in the outbound request module 330 for determining an active patient consent and an active sub-network exchange partner relationship contract effective between the requesting exchange partner and the determined sub-network or effective between the requesting exchange partner and the one or more responding exchange partners, may be configured to determine if a current date is within an effective date period in the patient consent and the relationship contract. In embodiments, this operation may comprise determining if there is a past consent for a past period, e.g., determining if there is a past consent for obtaining medication information for a patient from 6 months ago in another exchange partner. In embodiments, this operation may comprise determining if there is a consent that extends to the future or prohibits disclosure in the future, e.g., medication information may contain a consent for the future, psychological data may contain a prohibition.

In embodiments, the one or more computers may be configured with a delay queue process for stacking one or more transfers for a respective one of the exchange partners, when the respective exchange partner is unavailable or when a transfer exceeds a data limit, as noted for the operation 252 in FIG. 2.

In embodiments, a global identifier may be assigned based on the method called, a direction, a sub-network, and the exchange partners it is from and to. In embodiments, the global identifier may be transmitted to both the requesting exchange partner and the responding exchange partner and stored within the system.

In embodiments, the one or more computers may further be configured with a sharing module configured with a sub-process for receiving, via the one or more communications networks, a request for data sharing. In embodiments, the request for data sharing may be identified by the API used by the requesting exchange partner. In embodiments, the request for a sharing operation may be identified by or may be determined by data for the sub-network such as contracts applicable to the requesting and/or responding exchange partner. In embodiments, the request for data sharing may be identified by or may be determined by the given data being requested, e.g., there may be a flag in the data itself that the data may or may not be linked or may only be shared, or only disclosed to a given exchange partner using a sharing configuration, where data will not be stored at the requesting exchange partner and will not be updated.

In embodiments of the sharing module, it may further be configured with a sub-process for caching in a cache, by the one or more computers, the given data, a sub-process for receiving, via the one or more communications networks, a request for data sharing of the given data from a second exchange partner; and a sub-process for transmitting, by the one or more computers via the one or more communications networks, the given data to the second exchange partner from the cache; and a sub-process for transferring, by the one or more computers, via the one or more communications networks, the given data.

In embodiments, the one or more computers further may comprise a transportation module comprising a plurality transportation protocols. In embodiments, the sub-process to transmit may connect to the transportation module, which is configured to select a transportation protocol based at least in part on communications requirements of the responding exchange partner.

In embodiments, one or more of the patient consents in the master patient database may be limited, dynamically or statically, to specific data types, and the communications manager sub-process may be configured to determine whether there is a patient consent for the type of data requested in the request.

In embodiments, the one or more computers may further be configured with a push or pull process to automatically or manually transmit data updates using the global identifier, when triggered. In embodiments, the push process for the data may be triggered by the communications manager, or triggered by an API, or by data in the original request from an exchange partner, or by a flag or other indicator in the data, or detection of a data change. In embodiments, the updates could be performed automatically after a period of time has elapsed, e.g., every 15 minutes. In embodiments, the bad data could be corrected manually across the exchange partners.

In embodiments, the one or more computers further comprise a parsing module configured to parse an incoming request from an exchange partner, when it does not identify a method, and to select a method based on data in the incoming request. In embodiments, this selection operation may comprise selecting an API based on the data in the request. Such requests that do not necessarily identify a method may be received, for example, in an email, or in a Direct Message, or may be received in a file on a file server.

In embodiments, the method identified may be associated with one of the sub-networks, and the sub-process to create a communication manager sub-process creates a respective communication manager sub-process for each of a plurality of responding exchange partners and their one or more affiliated organizations.

In embodiments, the sub-process to create the global identifiers may only create a global identifier when the method determined is a predetermined method from a set of predetermined methods in the plurality of methods. Example methods in some embodiments may be API's to look at data, an API to request clinical notes, an API to request staff demographics or staff availability/appointment data, an API to request patient documentation, patient medication information. It is desirable to update such information in the requesting exchange partners in an ongoing basis as the data is changed.

Figure 4:
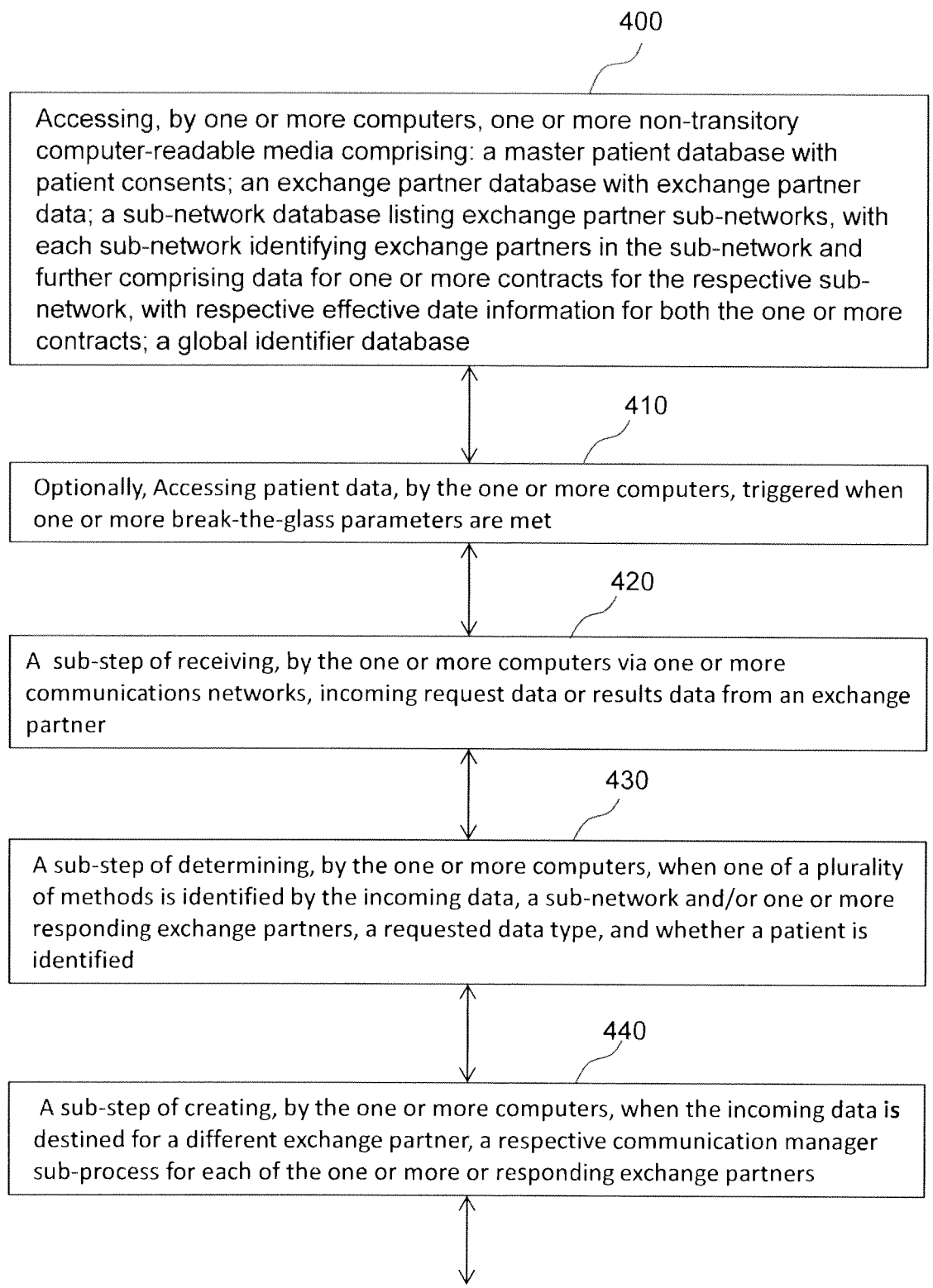
FIG. 4 illustrates an exemplary method embodiment for the invention.
Figure 4:
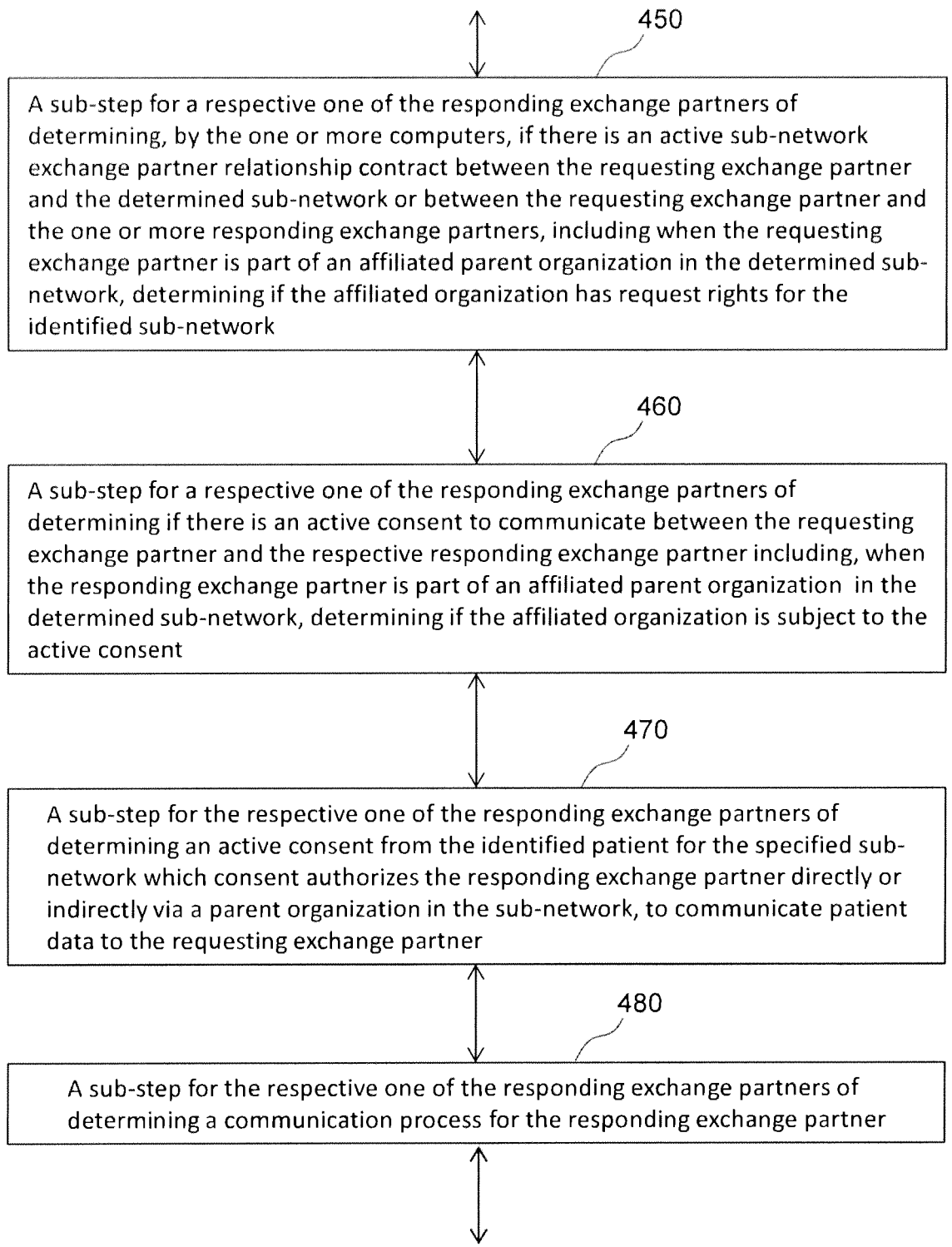
Figure 4:
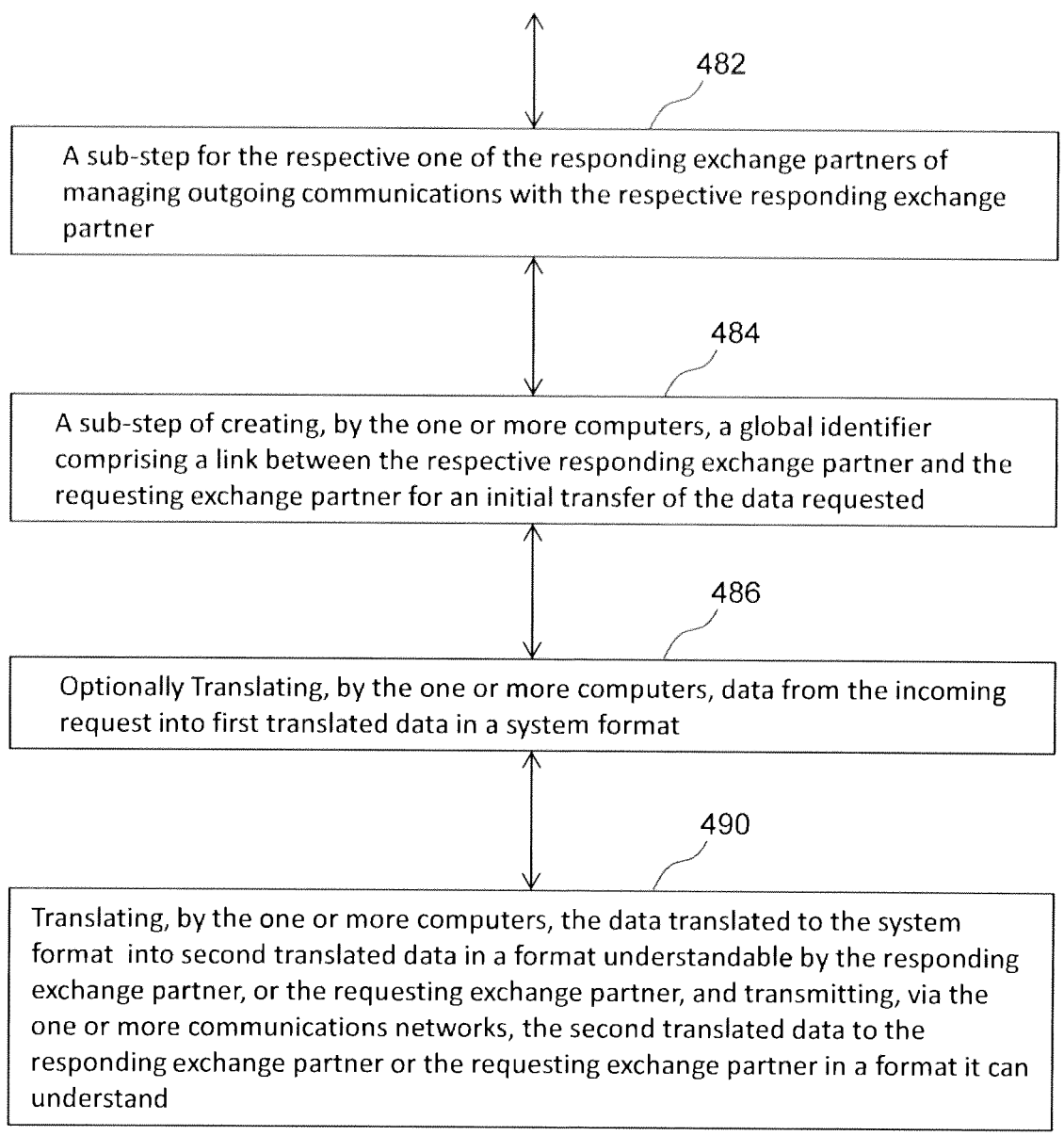

Referring to FIG. 4, embodiments of a method are disclosed. Block 400 comprises an operation of accessing, by one or more computers, one or more non-transitory computer-readable media comprising one or more of the databases: a master patient database with patient consents; an exchange partner database with exchange partner data; a sub-network database listing exchange partner sub-networks, with each sub-network identifying exchange partners in the sub-network and a set of common processes for communicating between the exchange partners in the respective sub-network, wherein the different sub-networks do not communicate with each other, and further comprising data for one or more contracts for the respective sub-network, with respective effective date information for both the one or more contracts and effective dates for respective patient consents for the respective sub-network or one or more exchange partners within the sub-network; and a global identifier database.

Block 410 comprises an optional operation that may be present in some embodiments of accessing patient data, by the one or more computers, triggered when one or more break-the-glass parameters are met.

Block 420 comprises an operation of receiving, by the one or more computers via one or more communications networks, incoming request data from a requesting exchange partner or results data from a responding exchange partner Block 430 comprises a sub-step of determining, by the one or more computers, when one of a plurality of methods is identified by the incoming data, a sub-network and/or one or more responding exchange partners, a requested data type, and whether a patient is identified.

Block 440 comprises a sub-step of creating, by the one or more computers, when the incoming data is destined for a different exchange partner, a respective communication manager sub-process for each of the one or more or responding exchange partners.

Block 450 comprises a sub-step for a respective one of the responding exchange partners of determining, by the one or more computers, if there is an active sub-network exchange partner relationship contract between the requesting exchange partner and the determined sub-network or between the requesting exchange partner and the one or more responding exchange partners, including when the requesting exchange partner is part of an affiliated parent organization in the determined sub-network, determining if the affiliated organization has request rights for the identified sub-network;

Block 460 comprises a sub-step for a respective one of the responding exchange partners of determining if there is an active consent to communicate between the requesting exchange partner and the respective responding exchange partner including, when the responding exchange partner is part of an affiliated parent organization in the determined sub-network, determining if the affiliated organization is subject to the active consent;

Block 470 comprises a sub-step for the respective one of the responding exchange partners of determining an active consent from the identified patient for the specified sub-network which consent authorizes the responding exchange partner directly or indirectly via a parent organization in the sub-network, to communicate patient data to the requesting exchange partner;

Block 480 comprises a sub-step for the respective one of the responding exchange partners of determining a communication process for the responding exchange partner.

Block 482 comprises a sub-step for the respective one of the responding exchange partners of managing outgoing communications with the respective responding exchange partner.

Block 484 comprises a sub-step of creating, by the one or more computers, a global identifier comprising a link between the respective responding exchange partner and the requesting exchange partner for an initial transfer of the data.

Block 486 comprises an optional sub-process to translate, by the one or more computers, data from the incoming request into first translated data in a system format, or translating results data from a responding exchange partner to a format that the requesting exchange partner can understand. Note that in some situations, one or more the exchange partners are using the same data formats as the system, e.g., the exchange partner is known to be sending data in a well-recognized, agreed upon format which the system understands with no translation necessary. For example if all exchange partners within a sub-network have agreed upon sending standardized data, then the present system may not need to perform any translation because the data is expected to be the same for and understood by all exchange partners involved. Thus, in this situation, no translation or mapping between data formats is required. In other situations, the exchange partners are using different data formats and translation between exchange partner data formats is required. In embodiments, this functionality may be in the inbound module.

Block 490 comprises a sub-process to translate, by the one or more computers, the data translated to the system format into second translated data in a format understandable by the responding exchange partner, or the requesting exchange partner, and to transmit, via the one or more communications networks, the second translated data to the responding exchange partner or the requesting exchange partner in a format it can understand. In embodiments, this functionality may be present in the outbound module.

The present system is designed to handle behavioral and physical health information to accommodate data, exchange partners, vendors, communication methods, and technical standards and consent standards that are constantly evolving and emerging. Rather than attempt to address one or more specific targets, the present system is designed to be flexible to accommodate the multitude of variations that may arise. Thus, for example, a system with only the capability of sending Direct messages may do so and have the message translated into a SOAP-compliant web service be sent to another system. This also allows the system to accommodate proprietary "semi-standards" of technology vendors.

The present system and method creates a health care information exchange that is highly consent-driven and can accommodate both physical health information and behavioral health information in the same system. At the core of the system is a powerful Data Routing Engine that evaluates numerous levels of legal relationships before allowing information to be routed to its destination including:

Exchange Partner Relationship—Has Agency A agreed to share information with Agency B?

Data Type Authority—Does Agency A's relationship with Agency B allow Agency B to access the type of requested data?

Consumer/Patient Consent—Does the system have a valid, non-expired consent on file that allows Agency A to share information with Agency B?

The increased privacy requirements surrounding behavioral health and substance use disorder information are frequently incompatible with the consent requirements of physical-health oriented systems.

To meet these needs, embodiments of the present invention are capable of transferring one or more of the following information among providers when the proper consents are confirmed:

Laboratory Test Results
Laboratory Orders
Medication List
Diagnosis List/Problem List
Allergies and Adverse Reactions
Vital Signs
Treatment Plan (IPOS)
Clinical Documents (PDF and/or structured)
CCR/CCD/CDA/C-CDA
Appointments/Schedule
Care Team
Secure Messaging between Care Team members
Secure Messaging between Care Team members and patients
Staff Service Activity Log
Demographics
Insurance Information
Admissions
Consents
HL7 v2.x/v3 Messaging
IHE Profile Messaging
NwIN/CONNECT Messaging Embodiments of the invention may be fully scalable in terms of data elements. Additional data elements may be implemented quickly and efficiently and added to this list based on the needs of exchange participants.

Within embodiments of the system, records for each staff within the sub-network may be stored. Each exchange partner within the sub-network may assign their own identifier to this staff record which is used to map that staff between exchange partners:

| Sub-Network Master Staff Index | | | | |
| --- | --- | --- | --- | --- |
| Staff Name | Internal The System Identifier | Exchange Partner A Identifier | Exchange Partner B Identifier | Exchange Partner C Identifier |
| Jack | 1 | | | 70 |
| Sarah | 2 | | 60 | |
| John | 3 | 50 | | 80 |

An example operation using the staff database may comprise the following: assume John at exchange partner A wishes to send a message to all staff within the sub-network that he operates within. John may select an API that results in a communication to the system to determine staff identifiers in the sub-network and their communications data. In this example, the system finds identifiers for Jack and Sarah. When the system sends the message to Jack, the data includes Jack's identifier 70 in the message because exchange partner C understands 70 to be Jack. When the system sends the message to Sarah, the data includes Sarah's identifier 60 because exchange partner B understands 60 to be Sarah. None of the receiving exchange partners need to know the internal identifier of staff in the other exchange partners in the sub-network.

This operation reduces overhead because each exchange partner involved may front-load the mapping information instead of passing it with each communication. Furthermore since the system performs the mappings, translation logic can be avoided at end-points. It is also more powerful because staff can be linked across exchange partners in the same way data is linked with global identifiers.

To generalize, in embodiments this same model of front-loading identifiers may be used with the master patient index, and is how the global identifiers for data communications operate, and how the data structure/data value mappings work.

In embodiments, the system may map data points and data the same way the system maps staff and global identifiers. For example, the system may store a data-point representing the language a patient speaks using respective identifiers from one or more exchange partners representing language:

Data Point Index

| Data Point | Internal The System Identifier | Exchange Partner A Identifier | Exchange Partner B Identifier | Exchange Partner C Identifier |
|---|---|---|---|---|
| Language | 1 | LANG | LNG | 100 |
| Date of Birth | 2 | DOB | DAOBIRTH | 200 |

And the system stores information which maps/translates the values for the language data-point:

Data Point Value Index for Language

| Value | Internal The System Identifier | Exchange Partner A Identifier | Exchange Partner B Identifier | Exchange Partner C Identifier |
|---|---|---|---|---|
| English | 1 | ENG | ENGLISH | 14 |
| Spanish | 2 | SPA | SPANISH | 17 |

The result is that embodiments of the system can receive the data LANG/ENG from exchange partner A, translate it to 100/14 and pass it to exchange partner C. Exchange partner C does not need to interpret/map "LANG" to "100" or "ENG" to 14.

In embodiments, the system provides the ability to manage consents. This includes the creation, revocation, modification, management, reconciliation, receipt, interpretation, and transmission of consent information. In embodiments, these activities may be performed using human-readable formats (e.g., JPEG or PDF), machine-readable formats (e.g., XACML, XML), or both. The communication of consent information (e.g., for receipt or transmission) may be in one or more standard or non-standard formats and may, generally, follow the data transmission and communications methods, policies, rules, formats, and protocols for other information as described elsewhere in this invention. In embodiments, the transmission and communication may be performed through a graphical user interface through which a human may interact, while in others, such transmission and communication may be performed through electronic interfaces and APIs in one or more formats (e.g., SOAP, secure FTP, DIRECT, etc.).

In embodiments, the system may interpret and logically consolidate consent information from one or more consents into a summary consent policy. A summary consent policy shows the effective consent policy that encompasses the combination of one or more consents. This summary consent policy may, in embodiments, provide a user or exchange partner with information regarding overlapping, conflicting, negating, or otherwise related consents. A summary consent policy may, in embodiments, provide a user or exchange partner with a consolidated policy on which data sharing may be performed. This may be used by users or exchange partners to effectively manage consents. Through configuration, the present system, in embodiments, can present information relating to the summary consent policy or, in other configurations, take action based on the information contained in the summary consent policy. For example, where a patient wishes to revoke a consent between exchange partner A and exchange partner B, the system may identify that another consent exists between exchange partner A and exchange partner C, which is a parent organization of exchange partner B, and which latter consent would continue to effectively allow the sharing of information between exchange partner A and exchange partner B. Depending on the configuration, the system may, for example, automatically revoke all of the applicable or conflicting consents, or request further guidance by presenting the additional consent to the user or requesting system, or, in other circumstances or configurations, the system could (automatically or through user or exchange partner intervention) create a negative consent that would override the A-to-C consent and prohibit the sharing of information between exchange partner A and exchange partner B, but continuing to allow the sharing of information between exchange partner A and C and C's other affiliates. In another example, a user could request all consents that relate to a particular exchange partner and the system could consolidate and present those consents (including consents for related exchange partners) and the policy that the combination of those consents effects. In yet another example, all consents may be displayed in a graphical user interface, and the effective policy based on the existing consents can be displayed. In this latter example, a user could "preview" the effect of creating, revoking, or otherwise modifying consents on the overall consolidated summary consent policy. This could be performed without actually completing the creation, revocation, or modification of consents unless and until the user decides to do so.

In embodiments, management of the consent may also include the identity verification and management of the consent and related signatures. In embodiments, consents may be printed and signatures can be obtained on "hard-copy" consents and scanned back into the system. In other embodiments, electronic signatures may be obtained directly from within the system or transmitted from a trusted exchange partner. In other embodiments, identity verification may be performed through an interface with a third party electronic identity verification/identity proofing system such as Experian.

The consolidated summary consent policy may in embodiments, be presented in formats that provide information to users, exchange partners, or patients regarding how the patient's information may flow among various exchange partners.

Many of the techniques described here may be implemented in hardware or software, or a combination of the two. Preferably, the techniques are implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Moreover, each program is preferably implemented in a high level procedural or object-oriented programming language to communicate with a computer system. However, the programs can be implemented in assembly or machine language, if desired. In embodiments, the language may be a compiled or interpreted language.

Each such computer program is preferably stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Figure 6:
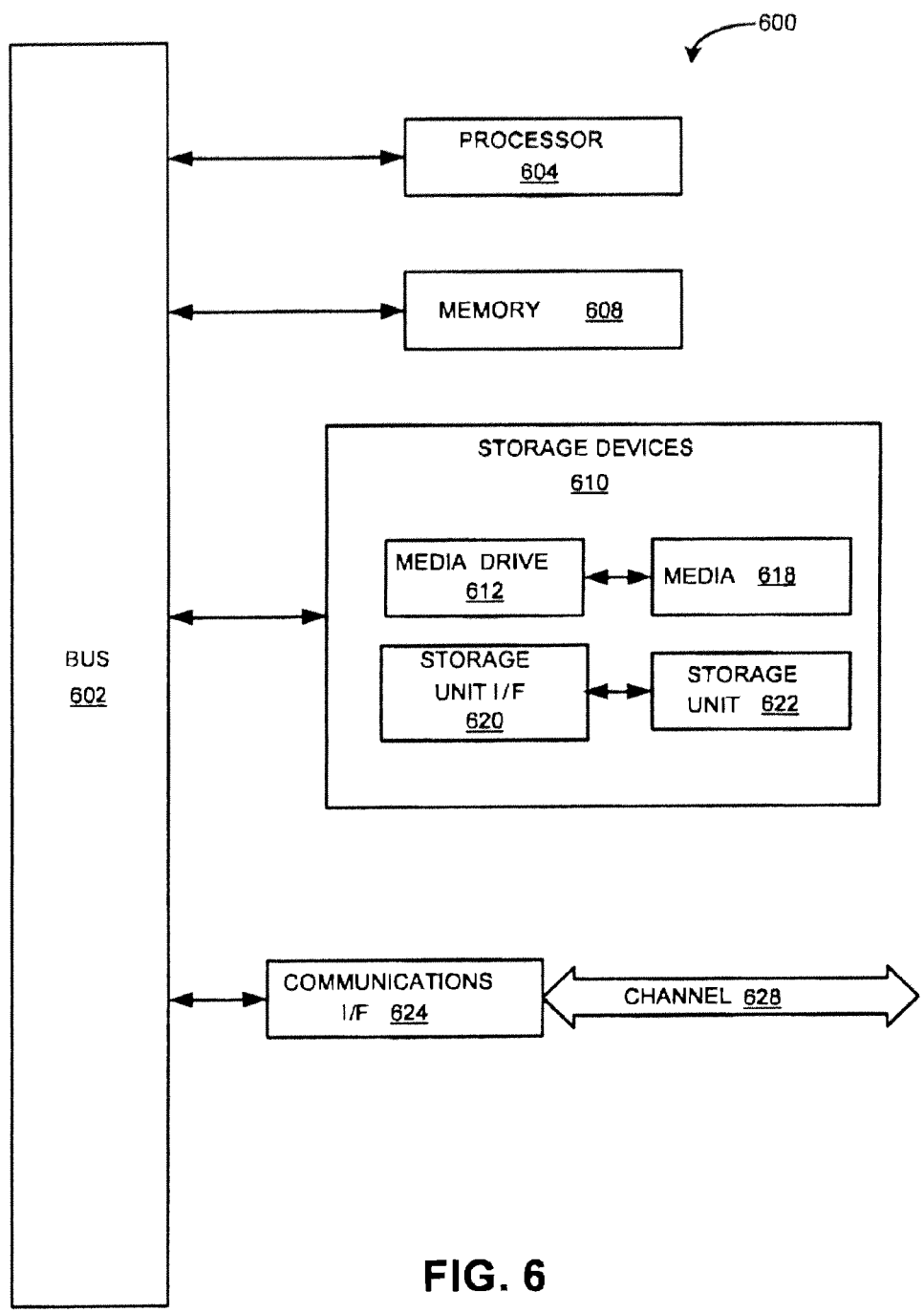
FIG. 6 is a system embodiment for implementing embodiments described herein.

FIG. 6 illustrates a typical computing system 600 that may be employed to implement processing functionality in embodiments of the invention. Computing systems of this type may be used in clients and servers, for example. Those skilled in the relevant art will also recognize how to implement the invention using other computer systems or architectures. Computing system 600 may represent, for example, a desktop, laptop or notebook computer, hand-held computing device (PDA, cell phone, palmtop, etc.), mainframe, server, client, or any other type of special or general purpose computing device as may be desirable or appropriate for a given application or environment. Computing system 600 can include one or more processors, such as a processor 604. Processor 604 can be implemented using a general or special purpose processing engine such as, for example, a microprocessor, microcontroller or other control logic. In this example, processor 604 is connected to a bus 602 or other communication medium.

Computing system 600 can also include a main memory 608, such as random access memory (RAM) or other dynamic memory, for storing information and instructions to be executed by processor 604. Main memory 608 also may be used for storing temporary variables or other intermediate information during execution of instructions to be executed by processor 604. Computing system 600 may likewise include a read only memory ("ROM") or other static storage device coupled to bus 602 for storing static information and instructions for processor 604.

The computing system 600 may also include information storage system 610, which may include, for example, a media drive 612 and a removable storage interface 620. The media drive 612 may include a drive or other mechanism to support fixed or removable storage media, such as a hard disk drive, a floppy disk drive, a magnetic tape drive, an optical disk drive, a CD or DVD drive (R or RW), or other removable or fixed media drive. Storage media 618 may include, for example, a hard disk, floppy disk, magnetic tape, optical disk, CD or DVD, or other fixed or removable medium that is read by and written to by media drive 612. As these examples illustrate, the storage media 618 may include a computer-readable storage medium having stored therein particular computer software or data.

In alternative embodiments, information storage system 610 may include other similar components for allowing computer programs or other instructions or data to be loaded into computing system 600. Such components may include, for example, a removable storage unit 622 and an interface 620, such as a program cartridge and cartridge interface, a removable memory (for example, a flash memory or other removable memory module) and memory slot, and other removable storage units 622 and interfaces 620 that allow software and data to be transferred from the removable storage unit 618 to computing system 600.

Computing system 600 can also include a communications interface 624. Communications interface 624 can be used to allow software and data to be transferred between computing system 600 and external devices. Examples of communications interface 624 can include a modem, a network interface (such as an Ethernet or other NIC card), a communications port (such as for example, a USB port), a PCMCIA slot and card, etc. Software and data transferred via communications interface 624 are in the form of signals which can be electronic, electromagnetic, optical or other signals capable of being received by communications interface 624. These signals are provided to communications interface 624 via a channel 628. This channel 628 may carry signals and may be implemented using a wireless medium, wire or cable, fiber optics, or other communications medium. Some examples of a channel include a phone line, a cellular phone link, an RF link, a network interface, a local or wide area network, and other communications channels.

In this document, the terms "computer program product," "computer-readable medium" and the like may be used generally to refer to physical, tangible media such as, for example, memory 608, storage media 618, or storage unit 622. These and other forms of computer-readable media may be involved in storing one or more instructions for use by processor 604, to cause the processor to perform specified operations. Such instructions, generally referred to as "computer program code" (which may be grouped in the form of computer programs or other groupings), when executed, enable the computing system 600 to perform features or functions of embodiments of the present invention. Note that the code may directly cause the processor to perform specified operations, be compiled to do so, and/or be combined with other software, hardware, and/or firmware elements (e.g., libraries for performing standard functions) to do so.

In an embodiment where the elements are implemented using software, the software may be stored in a computer-readable medium and loaded into computing system 600 using, for example, removable storage media 618, drive 612 or communications interface 624. The control logic (in this example, software instructions or computer program code), when executed by the processor 604, causes the processor 604 to perform the functions of the invention as described herein.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

It should be noted that although the flow charts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the invention. Likewise, software and web implementations of the present invention could be accomplished with programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations. It should also be noted that the phrase "a plurality" is intended to mean more than one, and is not intended to refer to any previous recitation of the word "plurality," unless preceded by the word "the." When it is stated that one of A and B, it means that one is selected from the group of A and B.

All components, modes of communication, and/or processes described heretofore are interchangeable and combinable with similar components, modes of communication, and/or processes disclosed elsewhere in the specification. It is intended that any structure or step of an embodiment disclosed herein may be combined with other structure and or method embodiments disclosed herein to form an embodiment with this added element or step, unless a statement herein explicitly prohibits this combination.

The above-described embodiments of the present invention are merely meant to be illustrative and not limiting. Various changes and modifications may be made without departing from the invention in its broader aspects. The appended claims encompass such changes and modifications within the spirit and scope of the invention.

We claim:

1. A system, comprising:
   memory comprising one or more non-transitory computer-readable media comprising:
      a master patient database with patient consents;
      an exchange partner database with exchange partner data;
      a sub-network database listing exchange partner sub-networks, with each sub-network identifying exchange partners in the sub-network and a set of common processes for communicating between the exchange partners in the respective sub-network, and further comprising data for one or more contracts for the respective sub-network, with respective effective date information for both the one or more contracts and effective dates for respective patient consents for the respective sub-network and/or one or more exchange partners within the sub-network; and
      a global identifier database storing a plurality of global identifiers;
   one or more computers comprising one or more processors, the computers configured with and the one or more processors configured to execute:
      an inbound module for receiving, by the one or more computers and the one or more communications networks, incoming request data or results data from an exchange partner, including the following sub-processes:
         a sub-process to receive, by the one or more computers via one or more communications networks, the incoming request data or results data from the exchange partner, the incoming request or results data from the exchange partner identifying a method that the exchange partner is attempting to call;
         a sub-process to determine, by the one or more computers, whether the exchange partner is authorized to call the method based on determining a sub-network and/or one or more responding exchange partners, a requested data type, and whether a patient is identified;
         a sub-process to create, by the one or more computers, when the incoming data is destined for a different exchange partner, a respective communication manager sub-process for each of the one or more or responding exchange partners;
      an outbound request module for processing, by the one or more computers, an incoming request from a requesting exchange partner or internal process to send/obtain data, with sub-processes comprising:
         the respective communication manager sub-process for a respective one of the responding exchange partners configured to determine, by the one or more computers, if there is an active sub-network exchange partner relationship contract between the requesting exchange partner and the determined sub-network or between the requesting exchange partner and the one or more responding exchange partners, including when the requesting exchange partner is part of an affiliated parent organization in the determined sub-network, determining if the affiliated organization has request rights for the identified sub-network;
         the respective communication manager sub-process for a respective one of the responding exchange partners configured to determine if there is an active consent to communicate between the requesting exchange partner and the respective responding exchange partner including, when the responding exchange partner is part of an affiliated parent organization in the determined sub-network, determining if the affiliated organization is subject to the active consent;
         the respective communication manager sub-process for the respective one of the responding exchange partners configured to determine an active consent from the specified patient for the specified sub-network which consent authorizes the responding exchange partner directly or indirectly via a parent organization in the sub-network, to communicate patient data to the requesting exchange partner, wherein the respective communication manager sub-process determines whether the requesting exchange partner may or may not request information from the responding exchange partner, and where it is determined that the requesting exchange partner may not request information from the responding exchange partner, the data request from the requesting exchange partner is denied, and any request, transaction, data, or communications is prevented from being routed or transmitted to the responding exchange partner, thereby physically protecting the responding exchange partner and its network or sub-network from receiving the such request, transaction, data, or communication made by the requesting exchange partner;
         the respective communication manager sub-process for the respective one of the responding exchange partners configured to determine a communication process for the responding exchange partner in the case where the requesting exchange partner is determined that it may request data from the responding exchange partner;
         the respective communication manager sub-process for the respective one of the responding exchange partners configured to manage outgoing communications with the respective responding exchange partner; and
         a sub-process to create, by the one or more computers, a global identifier comprising a link between the respective responding exchange partner and the requesting exchange partner for an initial transfer of the data,
   wherein the memory comprises a master staff index comprising for each of the exchange partners one or more staff; and
   wherein the one or more computers are further configured to access the master staff index and identify and map the communication to one or more of the staff identified via a respective staff identifier for the specified responding exchange partner, wherein the one or more computers are further configured with a process to transmit data updates using the global identifier, when triggered.

2. The system as defined in claim 1, wherein the one or more computers are configured with:
  a patient chart module for accessing patient data, with the patient chart module comprising a break-the-glass functionality for accessing patient data triggered when one or more parameters are met;
  a sub-process to translate, by the one or more computers, data from the incoming request into first translated data in a system format; and
  a sub-process to translate, by the one or more computers, the data translated to the system format into second translated data in a format understandable by the responding exchange partner, or the requesting exchange partner, and to transmit, via the one or more communications networks, the second translated data to the responding exchange partner or the requesting exchange partner in a format it can understand.

3. The system as defined in claim 1, wherein the sub-processes in the outbound request module for determining an active patient consent and an active sub-network exchange partner relationship contract effective between the requesting exchange partner and the determined sub-network or effective between the requesting exchange partner and the one or more responding exchange partners, determines if a date is within an effective date period in the patient consent and the relationship contract.

4. The system as defined in claim 1, wherein the one or more computers are further configured with a delay queue process for stacking one or more transfers for a respective one of the exchange partners, when the respective exchange partner is unavailable or when a transfer exceeds a data limit.

5. The system as defined in claim 1,
  wherein the global identifier is assigned based on the method called, a direction, and the exchange partners it is from and to, and
  wherein the global identifier is transmitted to both the requesting exchange partner and the responding exchange partner.

6. The system as defined in claim 1, further comprising a sharing module configured with the following sub-processes:
  a sub-process for receiving, via the one or more communications networks, a request for data sharing of given data from a first exchange partner;
  a sub-process for caching in a cache, by the one or more computers, the given data;
  a sub-process for receiving, via the one or more communications networks, a request for data sharing of the given data from a second exchange partner;
  a sub-process for transmitting, by the one or more computers via the one or more communications networks, the given data to the second exchange partner from the cache; and
  a sub-process for transferring, by the one or more computers, via the one or more communications networks, the given data.

7. The system as defined in claim 1, wherein the one or more computers further comprise a transportation module comprising a plurality transportation protocols, and wherein the sub-process to transmit connects to the transportation module, which is configured to select a transportation protocol based at least in part on communications requirements of the responding exchange partner.

8. The system as defined in claim 1, wherein one or more of the patient consents in the master patient database are limited, statically or dynamically, to specific data types; and
  wherein the communications manager sub-process is configured to determine whether there is a patient consent for the type of data requested in the request.

9. The system as defined in claim 1, wherein the one or more computers further comprise a parsing module configured to parse the incoming request, when it does not identify a method, and to select a method based on data in the incoming request.

10. The system as defined in claim 9, wherein the incoming request is contained in one selected from the group of an email, a Direct Message, a file in a file server.

11. The system as defined in claim 1, wherein the method identified is associated with one of the sub-networks, and wherein the sub-process to create a communication manager sub-process creates a respective communication manager sub-process for each of a plurality of responding exchange partners and their one or more affiliated organizations.

12. The system as defined in claim 1, wherein the sub-process to create the global identifiers only creates a global identifier when the identified method is a predetermined method from a set of predetermined methods.

13. The system as defined in claim 1, wherein the one or more computers are configured with a process to transmit data updates using the global identifier, when triggered by one or more parameters.

14. The system as defined in claim 1, wherein the different sub-networks do not communicate with each other unless there is data on a contract between the sub-networks.

15. The system as defined in claim 1, comprising an interface configured to create, revoke, modify, manage, reconcile, receive, interpret, or transmit the consents.

16. The system as defined in claim 1, wherein the one or more computers are configured to verify the identity of a person or entity through an electronic interface.

17. The system as defined in claim 15, wherein the interface comprises a graphical user interface.

18. The system as defined in claim 15, wherein the interface comprises one or more electronic interfaces or APIs for machine-to-machine interaction.

19. A method, comprising:
  accessing, by one or more computers comprising one or more processors, one or more non-transitory computer-readable media comprising:
    a master patient database with patient consents;
    an exchange partner database with exchange partner data;
    a sub-network database listing exchange partner sub-networks, with each sub-network identifying exchange partners in the sub-network and a set of common processes for communicating between the exchange partners in the respective sub-network, and further comprising data for one or more contracts for the respective sub-network, with respective effective date information for both the one or more contracts and effective dates for respective patient consents for the respective sub-network and/or one or more exchange partners within the sub-network; and
    a global identifier database;
  accessing data, by the one or more computers, triggered when one or more break-the-glass parameters are met;
  a sub-step of receiving, by the one or more computers via one or more communications networks, incoming request data or results data from an exchange partner, the incoming request or results data from the exchange partner identifying a communication method that the exchange partner is attempting to call;

a sub-step of determining, by the one or more computers, whether the exchange partner is authorized to call the method based on determining a sub-network and/or one or more responding exchange partners, a requested data type, and whether a patient is identified;

a sub-step of creating, by the one or more computers, when the incoming data is destined for a different exchange partner, a respective communication manager sub-process for each of the one or more or responding exchange partners;

processing, by the one or more computers, an incoming request from a requesting exchange partner or internal process to send/obtain data, with sub-processes comprising sub-steps:

a sub-step for a respective one of the responding exchange partners of determining, by the one or more computers, if there is an active sub-network exchange partner relationship contract between the requesting exchange partner and the determined sub-network or between the requesting exchange partner and the one or more responding exchange partners, including when the requesting exchange partner is part of an affiliated parent organization in the determined sub-network, determining if the affiliated organization has request rights for the identified sub-network;

a sub-step for a respective one of the responding exchange partners of determining if there is an active consent to communicate between the requesting exchange partner and the respective responding exchange partner including, when the responding exchange partner is part of an affiliated parent organization in the determined sub-network, determining if the affiliated organization is subject to the active consent;

a sub-step for the respective one of the responding exchange partners of determining an active consent from the identified patient for the specified sub-network which consent authorizes the responding exchange partner directly or indirectly via a parent organization in the sub-network, to communicate patient data to the requesting exchange partner, including determining whether the requesting exchange partner may or may not request information from the responding exchange partner, wherein, in the case where the request is determined that the requesting exchange partner may not request information from the responding exchange partner, the data request from the requesting exchange partner is denied, and preventing any request, transaction, data, or communications from being routed or transmitted to the responding exchange partner, thereby physically protecting the responding exchange partner and its network or sub-network from ever receiving the such request, transaction, data, or communication made by the requesting exchange partner;

a sub-step for the respective one of the responding exchange partners of determining a communication process for the responding exchange partner in the case where the requesting exchange partner is determined that it may request data from the responding exchange partner;

a sub-step for the respective one of the responding exchange partners of managing outgoing communications with the respective responding exchange partner;

a sub-step of creating, by the one or more computers, a global identifier comprising a link between the respective responding exchange partner and the requesting exchange partner for an initial transfer of the data;

a sub-step of accessing, by the one or more computers, a master staff index and identifying and mapping the communication to one or more of staff identified via a respective staff identifier for the specified responding exchange partner; and a sub-step of transmitting, by the one or more computers, data updates using the global identifier, when triggered by one or more parameters.

20. The method as defined in claim 19, further comprising:

translating, by the one or more computers, data from the incoming request into first translated data in a system format; and translating, by the one or more computers, the data translated to the system format into second translated data in a format understandable by the responding exchange partner, or the requesting exchange partner, and transmitting, via the one or more communications networks, the second translated data to the responding exchange partner or the requesting exchange partner in a format it can understand.

21. The method as defined in claim 19, wherein the steps for determining an active patient consent and an active sub-network exchange partner relationship contract effective between the requesting exchange partner determined sub-network or effective between the requesting exchange partner and the one or more responding exchange partners, comprise determining if a date is within an effective date period in the patient consent and the relationship contract.

22. The method as defined in claim 19, stacking in a delay queue, by the one or more computers, one or more transfers for a respective one of the exchange partners, when the respective exchange partner is unavailable or when a transfer exceeds a data limit.

23. The method as defined in claim 19, wherein the global identifier is assigned based on the method called, a direction, and the exchange partners it is from and to, and further comprising transmitting the global identifier, by the one or more computers, to both the requesting exchange partner and the responding exchange partner.

24. The method as defined in claim 19, receiving, via the one or more communications networks, a request for data sharing of given data from a first exchange partner;

caching in a cache, by the one or more computers, the given data;

receiving, via the one or more communications networks, a request for data sharing of the given data from a second exchange partner; and transmitting, by the one or more computers via the one or more communications networks, the given data to the second exchange partner from the cache; and transferring, by the one or more computers, via the one or more communications networks, the given patient data.

25. The method as defined in claim 19, wherein the transmitting steps comprise selecting, by the one or more computers, a transportation protocol based at least in part on communications requirements of the responding exchange partner.

26. The method as defined in claim 19, wherein one or more of the patient consents in the master patient database are limited to specific data types; and further comprising determining, by the one or more computers via access to the master patient database, whether there is a patient consent for the type of data requested in the request.

27. The method as defined in claim 19, parsing, by the one or more computers, the incoming request, when it does not identify a method, and selecting a method based on data in the incoming request.

28. The method as defined in claim 19, wherein step creating the global identifiers only creates a global identifier when the identified method is a predetermined method from a set of predetermined methods.

29. The method as defined in claim 19, further comprising accessing, by the one or more computers, one or more non-transitory computer-readable media comprising a patient consent database.

30. The method as defined in claim 29, further comprising transmitting consent information, via the one or more computers, in a standard or non-standard structured data format.

31. The method as defined in claim 29, further comprising transmitting consent information, via the one or more computers, in a human-readable image.

32. The method as defined in claim 29, further comprising receiving consent information, via the one or more computers, in a standard or non-standard structured data format, parsing the received consent and storing in the patient consent database, and making such received consent available for processing by the one or more computers.

33. The method as defined in claim 29, further comprising receiving consent information, via the one or more computers, in a human readable image, and making such received consent available to the one or more computers.

34. The method as defined in claim 30, further comprising receiving and parsing electronic requests for consent information, via the one or more computers, from an exchange partner and responding thereto.

35. The method as defined in claim 31, further comprising receiving and parsing electronic requests for consent information, via the one or more computers, from an exchange partner and responding thereto.

36. The method as defined in claim 29, further comprising revoking one or more consents at the request of a user or exchange partner which submits such request electronically through an electronic interface or through a human interaction with a graphical user interface with the one or more computers, and processing the revocation of such consents.

37. The method as defined in claim 36, wherein the revocation may be effective on one or more revocation criteria, which are specified through the revocation request or based on configured rules, through which the one or more computers may determine the consents that match the revocation criteria and revoke those matched consents.

38. The method as defined in claim 29, further comprising transmitting, via the one or more computers, a request, including a revocation request, to exchange partners.

39. The method as defined in claim 29, further comprising parsing, via the one or more computers, the consent information contained in the consent database, interpreting the parsed consent information, and logically consolidating the consent information in one or more formats.

40. The method as defined in claim 39, further comprising transmitting or displaying, via the one or more computers, the logically consolidated consent information.

41. The method as defined in claim 39, further comprising processing, via the one or more computers, one or more actions on one or more consents based on the logically consolidated consent information.

42. The system as defined in claim 1, wherein the master staff index for each of the exchange partners further comprise a staff identifier for each of the one or more staff, the staff identifier of a staff being different for each exchange partner.

43. The method as defined in claim 19, wherein the staff identifier is different for each exchange partner.

* * * * *